US012655109B2

(12) United States Patent
Alasibi et al.

(10) Patent No.: US 12,655,109 B2
(45) Date of Patent: Jun. 16, 2026

(54) PROCESS FOR PREPARING 5-FLUORO-4-IMINO-3-METHYL-1-(TOLUENE-4-SULFONYL)-3,4-DIHYDRO-1H-PYRIMIDIN-2-ONE

(71) Applicant: Adama Makhteshim Ltd., Beer Sheva (IL)

(72) Inventors: Samaa Alasibi, Hura (IL); Gal Suez, Dimona (IL); Eynat Matzner, Adi (IL)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 924 days.

(21) Appl. No.: 17/910,114

(22) PCT Filed: Mar. 9, 2021

(86) PCT No.: PCT/IB2021/051957
§ 371 (c)(1),
(2) Date: Sep. 8, 2022

(87) PCT Pub. No.: WO2021/181274
PCT Pub. Date: Sep. 16, 2021

(65) Prior Publication Data
US 2023/0104954 A1 Apr. 6, 2023

Related U.S. Application Data

(60) Provisional application No. 63/082,053, filed on Sep. 23, 2020, provisional application No. 62/986,883, filed on Mar. 9, 2020.

(51) Int. Cl.
*C07D 239/47* (2006.01)

(52) U.S. Cl.
CPC .................................. *C07D 239/47* (2013.01)

(58) Field of Classification Search
CPC .................................................... C07D 239/47
See application file for complete search history.

(56) References Cited

U.S. PATENT DOCUMENTS

| | | | |
|---|---|---|---|
| 8,318,758 | B2 | 11/2012 | Boebel |
| 8,470,839 | B2 | 6/2013 | Boebel |
| 8,552,020 | B2 | 10/2013 | Boebel |
| 8,916,579 | B2 | 12/2014 | Boebel |
| 9,000,002 | B2 | 4/2015 | Boebel |
| 9,006,259 | B2 | 4/2015 | Boebel |
| 9,271,497 | B2 | 3/2016 | Lorsbach |
| 9,321,734 | B2 | 4/2016 | Lorsbach |
| 9,526,245 | B2 | 12/2016 | Owen |
| 9,532,570 | B2 | 1/2017 | Owen |
| 9,538,753 | B2 | 1/2017 | Owen |

(Continued)

FOREIGN PATENT DOCUMENTS

| | | | |
|---|---|---|---|
| WO | WO 2023/166485 | A1 | 9/2023 |
| WO | WO 2023/228148 | A1 | 11/2023 |

(Continued)

OTHER PUBLICATIONS

International Search Report issued Nov. 5, 2021 in connection with PCT International Application No. PCT/IB2021/051957.

(Continued)

*Primary Examiner* — Rebecca L Anderson
(74) *Attorney, Agent, or Firm* — Gary J. Gershik

(57) ABSTRACT

The present invention provides a process for preparing the compound 5-fluoro-4-imine-3-methyl-1-(phenyl-4-sulfonyl)-3,4-dihydro-1H-pyrimidin-2-one having the formula (I):

(I)

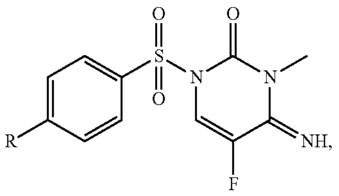

comprising (a) reacting 5-fluorocytosine with compound having the formula (III):

(III)

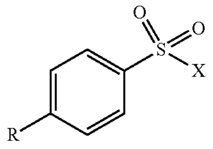

in the presence of at least one polar solvent and at least one base to obtain the compound having the formula (II)

(II)

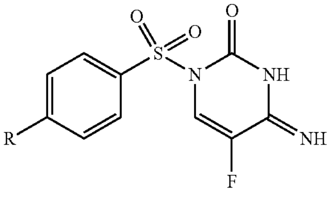

and (b) reacting compound having the formula (II) with dimethylsulphate (DMS), wherein R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$, and X is a halogen or —$OSO_2PhR$.

13 Claims, No Drawings

(56) References Cited

U.S. PATENT DOCUMENTS

| | | | |
|---|---|---|---|
| 9,622,474 | B2 | 4/2017 | Lorsbach |
| 9,642,368 | B2 | 5/2017 | Lorsbach |
| 9,840,475 | B2 | 12/2017 | Lorsbach |
| 9,840,476 | B2 | 12/2017 | Choy |
| 9,850,215 | B2 | 12/2017 | Choy |
| 9,862,686 | B2 | 1/2018 | Boebel |
| 9,908,855 | B2 | 3/2018 | Lorsbach |
| 10,045,533 | B2 | 8/2018 | Owen |
| 10,045,534 | B2 | 8/2018 | Owen |
| 10,051,862 | B2 | 8/2018 | Owen |
| 10,059,703 | B2 | 8/2018 | Lorsbach |
| 10,426,165 | B2 | 10/2019 | Owen |
| 10,426,166 | B2 | 10/2019 | Owen |
| 10,426,167 | B2 | 10/2019 | Owen |
| 10,919,864 | B2 | 2/2021 | Choy |
| 11,632,954 | B2 | 4/2023 | Grabarnick |
| 12,127,560 | B2 | 10/2024 | Owen |
| 2011/0263627 | A1 | 10/2011 | Boebel et al. |
| 2013/0045984 | A1 | 2/2013 | Boebel et al. |
| 2015/0183749 | A1 | 7/2015 | Choy et al. |
| 2022/0104490 | A1 | 4/2022 | Owen |
| 2022/0110323 | A1 | 4/2022 | Owen |
| 2022/0248673 | A1 | 8/2022 | Shabtai |
| 2023/0292746 | A1 | 9/2023 | Yardeni |
| 2024/0172750 | A1 | 5/2024 | Rosenmund |
| 2024/0237649 | A1 | 7/2024 | Giaffreda |
| 2024/0351990 | A1 | 10/2024 | Giaffreda |

FOREIGN PATENT DOCUMENTS

| | | | |
|---|---|---|---|
| WO | WO 2024/ 184859 | A1 | 9/2024 |
| WO | WO 2024/189563 | A1 | 9/2024 |
| WO | WO 2024/214047 | A1 | 10/2024 |

OTHER PUBLICATIONS

Notification of Transmittal of the International Search Report and the Written Opinion of the International Searching Authority, or the Declaration issued Nov. 5, 2021 in connection with PCT International Application No. PCT/IB2021/051957.

Ogilvie K. K et al., "The Alkylation of Purines, Pyrimidines and Nucleotides by Dialkyl Sulfates with Tetrabutylammonium Fluoride". Tetrahedron Letters, Elsevier, Amsterdam, NL, No. 35, Aug. 1, 1978, p. 3203-3206.

Whitehead, C. W. and Traverso, J. J., "Synthesis of Cytosines". Journal of the American Chemical Society, Nov. 20, 1955, vol. 77 (22), pp. 5867-5872.

Written Opinion of the International Searching Authority issued Nov. 5, 2021 in connection with PCT International Application No. PCT/IB2021/051957.

International Preliminary Report on Patentability issued Sep. 22, 2022, including Written Opinion of the International Searching Authority issued May 11, 2021, in connection with PCT International Application No. PCT/IB2021/051957.

PROCESS FOR PREPARING 5-FLUORO-4-IMINO-3-METHYL-1-(TOLUENE-4-SULFONYL)-3,4-DIHYDRO-1H-PYRIMIDIN-2-ONE

CROSS-REFERENCE TO RELATED APPLICATIONS

This application is a § 371 national stage of PCT International Application No. PCT/IB2021/051957, filed Mar. 9, 2021, claiming the benefit of U.S. Provisional Application Nos. 63/082,053 filed Sep. 23, 2020 and 62/986,883 filed Mar. 9, 2020, the entire contents of each of which are hereby incorporated by reference into the subject application.

Throughout this application various publications are referenced. The disclosures of these documents in their entireties are hereby incorporated by reference into this application in order to more fully describe the state of the art to which this invention pertains.

TECHNICAL FIELD

The present subject matter relates to an efficient procedure for preparing 5-fluoro-4-imino-3-methyl-1-(toluene-4-sulfonyl)-3,4-dihydro-1H-pyrimidin-2-one.

BACKGROUND

The compound 5-fluoro-4-imino-3-methyl-1-(toluene-4-sulfonyl)-3,4-dihydro-1H-pyrimidin-2-one has the structure:

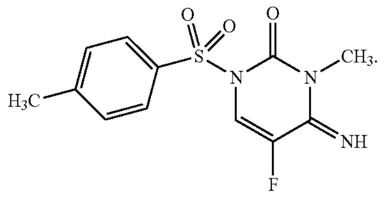 [SMILES: Cc1ccc(S(=O)(=O)n2cc(F)c(=N)n(C)c2=O)cc1]

5-fluoro-4-imino-3-methyl-1-(toluene-4-sulfonyl)-3,4-dihydro-1H-pyrimidin-2-one is a systemic fungicide which provides control of variety of pathogens in economically important crops including, but not limited to, the causal agent of leaf blotch in wheat, *Septoria tritici* (SEPTTR).

Different manufacturing processes are known from the literature, including those described in WO 2015/103144 and WO 2015/103142. There is a need to develop a more efficient synthesis pathway in terms of costs, yield, conversion and purity.

SUMMARY OF THE INVENTION

The present invention provides a process for preparing the compound 5-fluoro-4-imino-3-methyl-1-(phenyl-4-sulfonyl)-3,4-dihydro-1H-pyrimidin-2-one having the formula (I):

(I)

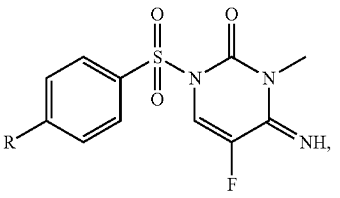

comprising (a) reacting 5-fluorocytosine with compound having the formula (III):

(III)

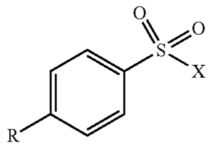

in the presence of at least one polar solvent and at least one base to obtain the compound having the formula (II)

(II)

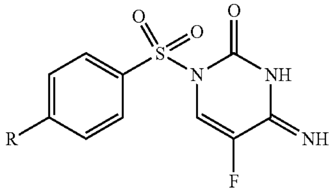

and (b) reacting compound having the formula (II) with dimethylsulphate (DMS);

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, $—NH_2$, $—NO_2$, —CN or $CF_3$; and X is a halogen or $—OSO_2PhR$.

In some embodiment, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, $—NH_2$, $—NO_2$, —CN or In some embodiments, the compound having the formula (I) is (Ia) wherein R is alkyl.

In some embodiments, the compound having the formula (Ta) is (Iai) wherein R is methyl.

The present invention provides a process for preparing the compound 5-fluoro-4-imino-3-methyl-1-(toluene-4-sulfonyl)-3,4-dihydro-1H-pyrimidin-2-one having the formula (Iai):

(Iai)

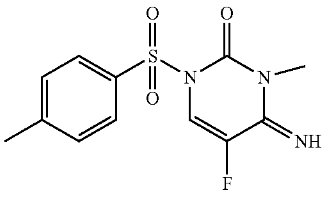

comprising (a) reacting 5-fluorocytosine with compound having the formula (III):

(III)

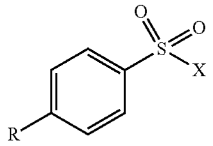

in the presence of at least one polar solvent and at least one base to obtain the compound having the formula (IIai)

and (IIai)

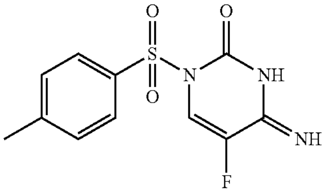

(b) reacting compound having the formula (IIai) with dimethylsulphate (DMS);

wherein R is methyl and X is a halogen or —$OSO_2PhR$.

The present invention provides a process for preparing the compound 5-fluoro-4-imino-1-(phenyl-4-sulfonyl)-3,4-dihydro-1H-pyrimidin-2-one having the formula (II):

(II)

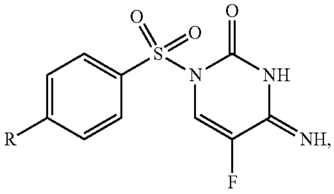

comprising (a) reacting 5-fluorocytosine with compound having the formula (III):

(III)

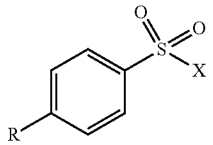

in the presence of at least one polar solvent and at least one base;

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$;

and X is a halogen or —$OSO_2PhR$.

In some embodiments, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, the compound having the formula (II) is (IIa) wherein R is alkyl.

In some embodiments, the compound having the formula (IIa) is (IIai) wherein R is methyl.

The present invention provides a process for preparing the compound 5-fluoro-4-imino-3-methyl-1-(phenyl-4-sulfonyl)-3,4-dihydro-1H-pyrimidin-2-one having the formula (I):

(I)

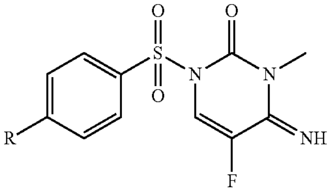

comprising (a) reacting compound having the formula (II)

(II)

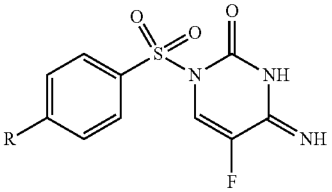

with dimethylsulphate (DMS);

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, the compound having the formula (I) is (Ia) wherein R is alkyl.

In some embodiments, the compound having the formula (Ia) is (Iai) wherein R is methyl.

The present invention further provides a process for preparing the compound 5-fluoro-4-imino-1-(toluene-4-sulfonyl)-3,4-dihydro-1H-pyrimidin-2-one having the formula (IIai)

(IIai)

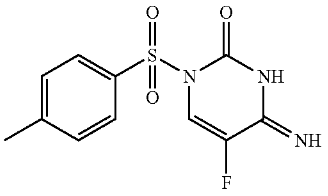

comprising (a) reacting 5-fluorocytosine with compound having the formula (III):

(III)

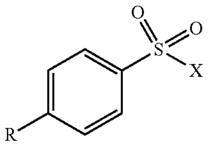

in the presence of at least one polar solvent and at least one base to obtain the compound having the formula (IIai)

(IIai)

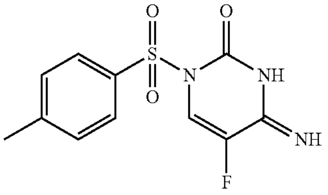

wherein R is methyl and X is a halogen or $-OSO_2PhR$.

The present invention provides a process for preparing the compound 5-fluoro-4-imino-3-methyl-1-(toluene-4-sulfonyl)-3,4-dihydro-1H-pyrimidin-2-one having the formula (Iai)

(Iai)

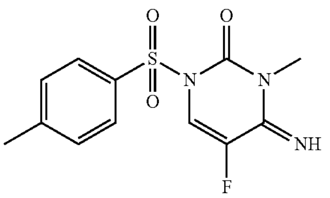

comprising reacting compound 5-fluoro-4-imino-1-(toluene sulfonyl)-3,4-dihydro-1H-pyrimidin-2-one having the formula (IIai)

(IIai)

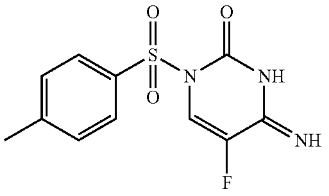 [SMILES: Cc1ccc(S(=O)(=O)n2cc(F)c(=N)[nH]c2=O)cc1]

with dimethylsulphate (DMS).

The present invention provides a method for isolating a compound having formula (I) from a mixture thereof, the method comprising contacting the mixture comprising the compound having formula (I) with a solvent or a mixture of solvents and filtering the precipitated solid.

The present invention provides a method for isolating compound having the formula (I) comprising (1) washing of an organic solution comprising a polar water immiscible solvent and a mixture of compound (I) and DMS with 2-15% w/w of aqueous basic solution, (2) separating the organic phase from the water phase, and (3) concentrating the organic phase and filtering the precipitated solid.

The present invention provides a method for isolating the compound having the formula (I) from a mixture comprising the compound having formula (I) and DMS, wherein the method comprises (1) dissolving the mixture comprising the compound having formula (I) and DMS in an organic polar solvent to obtain an organic solution, (2) washing the organic solution obtained from (1) with 2-15% w/w of aqueous basic solution, (3) separating the organic phase from the water phase, and (4) concentrating the organic phase and filtering the precipitated solid.

The present invention provides a method for isolating the compound having formula (I) from a mixture comprising the compound having formula (I) and DMS, wherein the method comprises (1) mixing the mixture comprising (i) the compound having formula (I), (ii) DMS and optionally (iii) a solvent with 2-15% w/w of an aqueous basic solution to obtain slurry mixture containing solids, and (2) filtering the precipitated solids.

In some embodiments, the compound having the formula (I) is (Ia) wherein R is alkyl.

In some embodiments, the compound having the formula (Ia) is (Iai) wherein R is methyl.

DETAILED DESCRIPTION OF THE INVENTION

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of". In each such instance, the terms "comprising," "consisting essentially of," and "consisting of" are intended to have the same meaning as each such term would have when used as the transition phrase of a patent claim.

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, use of the term "about" herein specifically includes ±10% from the indicated values in the range. Use of the term "about" herein more specifically includes ±1% from the indicated values in the range. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

In addition, the endpoints of all ranges directed to the same component or property herein are inclusive of the endpoints, are independently combinable, and include all intermediate points and ranges. Where a range is given in the specification it is understood that the range includes all integers and 0.1 units within that range, and any sub-range thereof. For example, a range of "77 to 90%" is a disclosure of 77.0%, 70.1%, 77.2%, 77.3% etc. up to 90%.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on.

As used herein, "alkoxy" represents an alkyl group as described above attached through an oxygen bridge.

As used herein, "Ph" is referring to phenyl group.

As used herein, the term "soluble" means when 1 g of substance is dissolved in the approximate volume of 100 ml.

As used in describing the tosylation step, the term "polar solvent" refers to solvent which has a dielectric constant equal to or above 20. As used in the remaining application, including in describing the sulfonation step other than tosylation step, the alkylation step and the isolation step, the term "polar solvent" has the meaning commonly understood by one of skill in the art to which this subject matter pertains, and includes, but is not limited to, solvent which has a dielectric constant equal to or above 20.

The polar solvent used in each of the sulfonation step, the alkylation step and isolation step may be the same or different. When the sulfonation step is a tosylation step, the polar solvent has a dielectric constant equal to or above 20.

As used herein, the term "formula (II)" refers to the following structure:

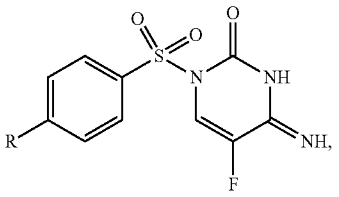

wherein R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$, and tautomers thereof, including but not limited to enamine tautomers thereof.

As used herein, the term "formula (IIai)" refers to the following structure:

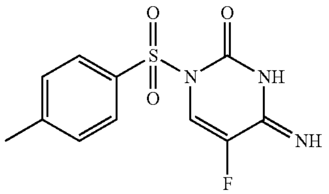

and tautomers thereof, including but not limited to an enamine tautomer thereof. For example, the compound having formula (IIai) includes both of the following compounds:

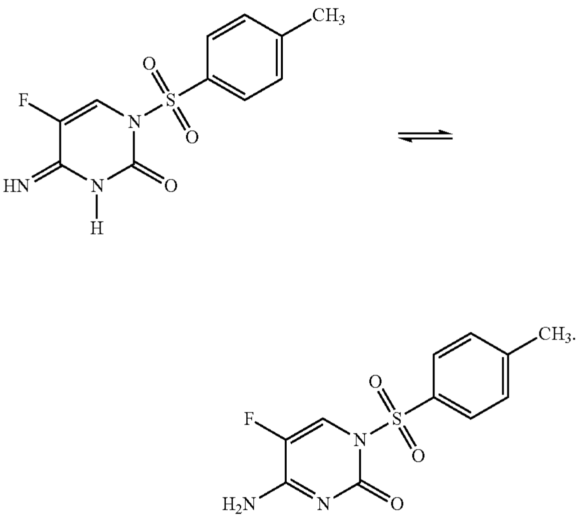

Preparing the compound (I) in an efficient procedure is a challenge. The preparation includes two step reaction of sulfonation and alkylation.

Lack of selectivity in preparation of compound (II) refers to formation impurities such as compound having the formula [A] and compound having the formula [B].

A

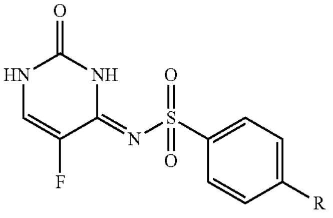

B

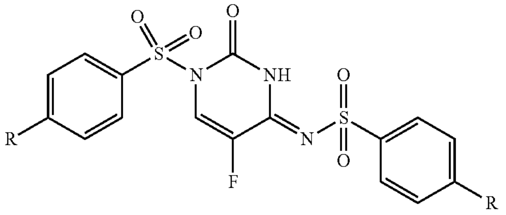

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid, halogen, —SH, —OH, —$NH_2$, —$NO_2$, —CN or $CF_3$.

The known processes in WO 2015/103144 and WO 2015/103142 include (1) a tosylation process of 5-fluorocytosine using bis-N,O-trimethylsilylacetamide (BSA) and (2) methylation process in the presence of a base which is prone to forming by-products.

It was found that preparing the compound having the structure (I) in specific conditions provides a selective and effective process.

The present invention provides a process for preparing the compound 5-fluoro-4-imino-3-methyl-1-(phenyl-4-sulfonyl)-3,4-dihydro-1H-pyrimidin-2-one having the formula (I):

(I)

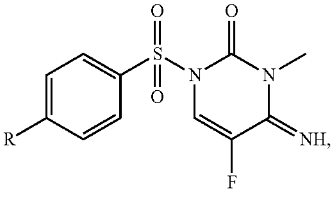

comprising (a) reacting 5-fluorocytosine with compound having the formula (III):

(III)

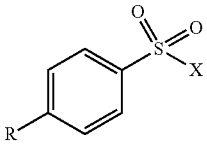

in the presence of at least one polar solvent and at least one base to obtain the compound having the formula (II)

(II)

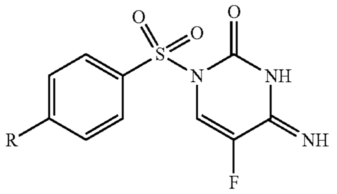

and (b) reacting compound having the formula (II) with dimethylsulphate (DMS);

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$;

and X is a halogen or —$OSO_2PhR$.

In some embodiments, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, the compound having the formula (I) is (Ia) wherein R is alkyl.

In some embodiments, the compound having the formula (Ia) is (Iai) wherein R is methyl.

The present invention provides a process for preparing the compound 5-fluoro-4-imino-3-methyl-1-(toluene-4-sulfonyl)-3,4-dihydro-1H-pyrimidin-2-one having the formula (Iai):

(Iai)

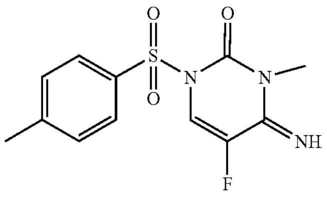

comprising (a) reacting 5-fluorocytosine with compound having the formula (III):

(III)

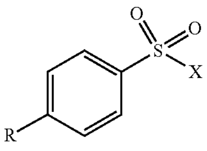

in the presence of at least one polar solvent and at least one base to obtain the compound having the formula (IIai)

and (IIai)

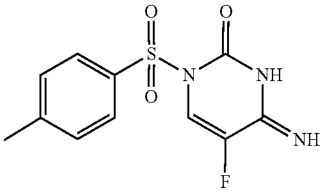

(b) reacting compound having the formula (IIai) with dimethylsulphate (DMS);

wherein R is methyl and X is a halogen or —$OSO_2PhR$.

The present invention provides a process for preparing the compound 5-fluoro-4-imino-1-(phenyl-4-sulfonyl)-3,4-dihydro-1H-pyrimidin-2-one having the formula (II):

(II)

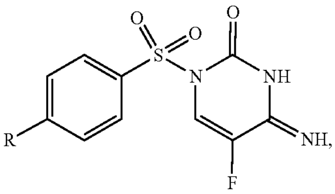

comprising reacting 5-fluorocytosine with compound having the formula (III):

(III)

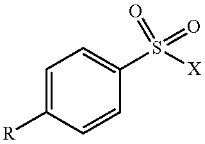

in the presence of at least one polar solvent and at least one base, wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$;

and X is a halogen or —$OSO_2PhR$.

In some embodiments, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NO_2$, —CN or $CF_3$.

In some embodiments, the compound having the formula (II) is (IIa) wherein R is alkyl.

In some embodiments, the compound having the formula (IIa) is (IIai) wherein R is methyl.

The present invention provides a process for preparing the compound 5-fluoro-4-imino-3-methyl-1-(phenyl-4-sulfonyl)-3,4-dihydro-1H-pyrimidin-2-one having the formula (I):

(I)

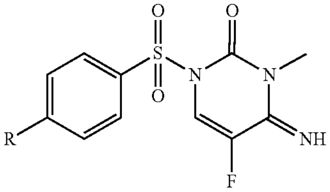

comprising reacting compound having the formula (II)

(II)

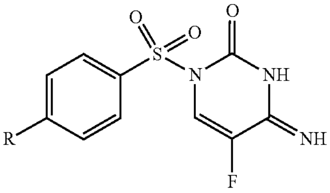

with dimethylsulphate (DMS);

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, the compound having the formula (I) is (Ia) wherein R is alkyl.

In some embodiments, the compound having the formula (Ia) is (Iai) wherein R is methyl.

The present invention further provides a process for preparing the compound 5-fluoro-4-imino-1-(toluene-4-sulfonyl)-3,4-dihydro-1H-pyrimidin-2-one having the formula (IIai)

(IIai)

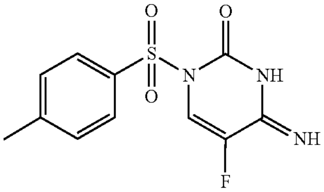

comprising reacting 5-fluorocytosine with compound having the formula (III):

(III)

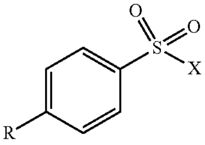

in the presence of at least one polar solvent and at least one base to obtain the compound having the formula (IIai)

(IIai)

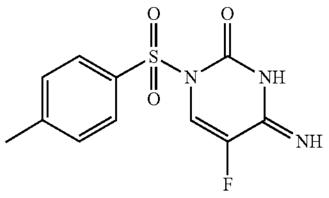

wherein R is methyl and X is a halogen or —$OSO_2PhR$.

The present invention provides a process for preparing the compound 5-fluoro-4-imino-3-methyl-1-(toluene-4-sulfonyl)-3,4-dihydro-1H-pyrimidin-2-one having the formula (Iai)

(Iai)

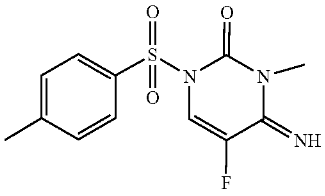

comprising reacting compound 5-fluoro-4-imino-1-(toluene-4-sulfonyl)-3,4-dihydro-1H-pyrimidin-2-one having the formula (IIai)

(IIai)

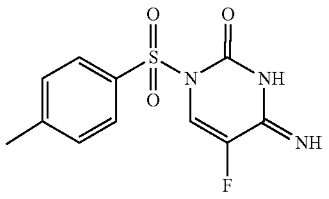

with dimethylsulphate (DMS).

Reacting 5-Fluorocytosine with Compound Having the Formula (III) (the Sulfonation Step)

As described above, the present invention includes reacting 5-fluorocytosine with the compound having formula (III). The compound having formula (III) is defined hereinabove.

In some embodiments, the reaction of 5-fluorocytosine with the compound having formula (III) is carried out in the absence of protecting group.

In some embodiments, X is a halogen. In some embodiments, the halogen is Cl, Br or I. In some embodiments, the halogen is Cl.

In some embodiments, X is —$OSO_2PhR$, wherein R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —ON or $CF_3$.

In some embodiments, X is

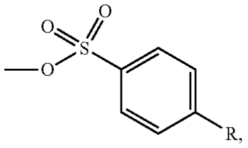

wherein R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —ON or $CF_3$.

In some embodiments, the compound having formula (III) is a compound having formula (IIIb)

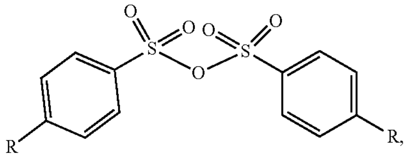

wherein R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$. In some embodiments, X is —$OSO_2PhR$ and R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, R is alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$.

In some embodiments, R is alkyl.

In some embodiments, the compound having formula (III) is toluenesulfonyl anhydride.

In some embodiments, the compound having the formula (III) may include but is not limited to 4-toluenesulfonyl chloride (TsCl) and toluenesulfonyl anhydride.

In some embodiments, the compound having the formula (III) is 4-toluenesulfonyl chloride (TsCl). In some embodiments, the compound having the formula (III) is toluenesulfonyl anhydride.

In some embodiments, the reaction of 5-fluorocytosine with the compound having the formula (III) is conducted at a temperature between (−5)-85° C. In some embodiments, the reaction of 5-fluorocytosine with the compound having the formula (III) is conducted at temperature between (−5)–25° C. In some embodiments, the reaction of 5-fluorocytosine with the compound having the formula (III) is conducted at temperature between (−5)–5° C. In some embodiments, the reaction of 5-fluorocytosine with the compound having the formula (III) is conducted at temperature between (−5)-0° C. In some embodiments, the reaction of 5-fluorocytosine with the compound having the formula (III) is conducted at temperature between 0-5° C. In some embodiments, the reaction of 5-fluorocytosine with the compound having the formula (III) is conducted at temperature between 5-25° C. In some embodiments, the reaction of 5-fluorocytosine with the compound having the formula (III) is conducted at temperature between 25-85° C. In some embodiments, the reaction of 5-fluorocytosine with the compound having the formula (III) is conducted in the presence of at least one polar solvent and at least one base.

In some embodiments, the reaction of 5-fluorocytosine with the compound having the formula (III) is conducted in the presence of at least one polar solvent, at least one base and at a temperature between 0-5° C. In some embodiments, the reaction of 5-fluorocytosine with the compound having the formula (III) is conducted in the presence of two polar solvents, one base and at a temperature between 0-5° C.

In some embodiments, the reaction of 5-fluorocytosine with the compound having the formula (III) is conducted in the presence of at least one polar solvent, at least one base and at a temperature between 5-25° C.

In some embodiments, the reaction of 5-fluorocytosine with the compound having the formula (III) is conducted in the presence of a polar solvent, at least one base and at a temperature between 25-85° C.

In some embodiments, the reaction of 5-fluorocytosine with compound having the formula (III) is conducted in the presence of at least one polar solvent, at least one base and at a temperature between (−5)–85° C.

In some embodiments, the polar solvent has a dielectric constant equal to or above 5. In some embodiments, the polar solvent has a dielectric constant equal to or above 10. In some embodiments, the polar solvent has a dielectric constant equal to or above 15. In some embodiments, the polar solvent has a dielectric constant equal to or above 20.

In some embodiments, wherein R is methyl in the compound having formula (III), the sulfonation step is a tosylation step.

In the tosylation step, the polar solvent has a dielectric constant equal to or above 20.

In some embodiments, the polar solvent having dielectric constant equal to or above 20 may include but is not limited to dimethyl acetamide (DMA), N-methylpyrolidone (NMP), acetonitrile (ACN or MeCN), dimethylsulfoxide (DMSO), dimethylformamide (DMF), water or any combination thereof.

In some embodiments, the polar solvent is selected from the group consisting of dimethyl acetamide (DMA), N-methylpyrolidone (NMP), acetonitrile (ACN or MeCN), dimethylsulfoxide (DMSO), dimethylformamide (DMF), dimethylbenzylamine (DMBA), water and any combination thereof.

In some embodiments, the polar solvent is selected from the group consisting of dimethyl acetamide (DMA), acetonitrile (ACN or MeCN), dimethylbenzylamine (DMBA), water and any combination thereof.

In some embodiments the combination of polar solvent and base consist of one phase system.

In some embodiments, the reaction of 5-fluorocytosine with the compound having the formula (III) is conducted in the presence of one polar solvent.

In some embodiments, the reaction of 5-fluorocytosine with the compound having the formula (III) is conducted in the presence of two polar solvents.

In some embodiments, the two polar solvents are selected from the group consisting of dimethyl acetamide (DMA), N-methylpyrolidone (NMP), acetonitrile (ACN or MeCN), dimethylsulfoxide (DMSO), dimethylformamide (DMF), dimethylbenzylamine (DMBA), and water.

In some embodiments, the two polar solvent are selected from the group consisting of dimethyl acetamide (DMA), acetonitrile (ACN or MeCN), dimethyl aminopyridine (DMAP), and water.

In some embodiments, the two polar solvents are DMA and water.

In some embodiments, the weight ratio between the two polar solvents is between 10:1 to 1:10.

In some embodiments, the weight ratio between the two polar solvents is between 2:1 to 1:2.

In some embodiments, the weight ratio between the two polar solvents is 1:1.

In some embodiments, the reaction of 5-fluorocytosine with the compound having the formula (III) is conducted in the presence of three polar solvents.

In some embodiments, the three polar solvents are DMA, water and DMBA.

In some embodiments, at least one base is an organic base.

In some embodiments, at least one base is an inorganic base.

In some embodiments, the reaction of 5-fluorocytosine with the compound having the formula (III) is conducted in the presence of one base.

In some embodiments, the reaction of 5-fluorocytosine with the compound having the formula (III) is conducted in the presence of two bases.

In some embodiments, the base may include but is not limited to $K_2CO_3$, $Na_2CO_3$, $Li_2CO_3$, $NaHCO_3$, $KHCO_3$, NaOH, KOH, $Et_3N$, dimethyl aminopyridine (DMAP), dimethylbenzylamine (DMBA) or any combination thereof.

In some embodiments, the base is selected from a group consisting of $K_2CO_3$, $Na_2CO_3$, $Li_2CO_3$, $NaHCO_3$, $KHCO_3$, $Et_3N$, dimethyl aminopyridine (DMAP) and any combination thereof.

In some embodiments, the base is selected from the group consisting of $K_2CO_3$, $Na_2CO_3$, NaOH, KOH, $Et_3N$, dimethyl aminopyridine (DMAP), and any combination thereof.

In some embodiments, the base is $K_2CO_3$. In some embodiments, the base is $Na_2CO_3$. In some embodiments, the base is NaOH. In some embodiments, the base is KOH, In some embodiments, the base is $Et_3N$, In some embodiments, the base is DMAP In some embodiments, the reaction of 5-fluorocytosine with the compound having the formula (III) is conducted in the presence of a DMA and at least one base.

In some embodiments, the reaction of 5-fluorocytosine with the compound having the formula (III) is conducted in the presence of a DMA, water and at least one base. In some embodiments, the reaction of 5-fluorocytosine with the compound having the formula (III) is conducted in the presence of a DMA, water and one base.

In some embodiments, the reaction of 5-fluorocytosine with the compound having the formula (III) is conducted in the presence of a DMA, water and two bases.

In some embodiments, the reaction of 5-fluorocytosine with the compound having the formula (III) is conducted in the presence of a DMA and two bases.

In some embodiments, the two bases are $Et_3N$ and DMAP.

In some embodiments, the two bases are NaOH and DMAP.

In some embodiments, the two bases are dimethylbenzylamine and NaOH.

In some embodiments, the two bases are DMAP and $Na_2CO_3$.

In some embodiments, the two bases are DMAP and KOH.

In some embodiments, the reaction of 5-fluorocytosine with the compound having the formula (III) is conducted in the presence of DMA, water and $K_2CO_3$.

In some embodiments, the reaction of 5-fluorocytosine with the compound having the formula (III) is conducted in the presence of DMA and $Et_3N$.

In some embodiments, the reaction of 5-fluorocytosine with the compound having the formula (III) is conducted in the presence of acetonitrile (ACN or MeCN) and triethylamine ($Et_3N$).

In some embodiments, the reaction of 5-fluorocytosine with the compound having the formula (III) is conducted in the presence of DMA, water and DMAP.

In some embodiments, the reaction of 5-fluorocytosine with the compound having the formula (III) is conducted in the presence of DMA and $Na_2CO_3$.

In some embodiments, the reaction of 5-fluorocytosine with the compound having the formula (III) is conducted in the presence of DMBA and $Na_2CO_3$.

In some embodiments, the reaction of 5-fluorocytosine with the compound having the formula (III) is conducted in the presence of water and DMAP.

In some embodiments, the reaction of 5-fluorocytosine with the compound having the formula (III) is conducted in the presence of DMBA, DMA, water and KOH.

In some embodiments, the reaction of 5-fluorocytosine with the compound having the formula (III) is conducted in the presence of DMBA, DMA, water and NaOH.

In some embodiments, the reaction of 5-fluorocytosine with the compound having the formula (III) is conducted in the presence of a DMA, $Et_3N$ and DMAP.

In some embodiments, the reaction of 5-fluorocytosine with the compound having the formula (III) is conducted in the presence of a DMA, water, NaOH and DMAP.

In some embodiments, the reaction of 5-fluorocytosine with the compound having the formula (III) is conducted in the presence of DMAP and $Na_2CO_3$.

In some embodiments, the reaction of 5-fluorocytosine with the compound having the formula (III) is conducted in the presence of DMBA and KOH In some embodiments, the reaction of 5-fluorocytosine with the compound having the formula (III) is conducted in the presence of DMBA and NaOH.

In some embodiments, the polar solvent has a dielectric constant equal to or above 20 is DMA, and the base is $Et_3N$.

In some embodiment, the polar solvent has a dielectric constant equal to or above 20 is mixture of DMA and water, and the base is $K_2CO_3$.

In some embodiments, the polar solvent has a dielectric constant equal to or above 20 is water, the base is $Et_3N$ and the temperature is (−5)-5° C.

In some embodiments, the temperature is (−5)-5° C., and the solvent is acetonitrile.

In another preferred embodiment, the temperature is (−5)-5° C., the solvent is acetonitrile, and the base is $Et_3N$.

In some embodiments, in the reaction of 5-fluorocytosine with the compound having formula (III), the molar ratio between 5-fluorocytosine and the compound having formula (III) is between 1:10 to 10:1. In some embodiments, in the reaction of 5-fluorocytosine with the compound having formula (III), the molar ratio between 5-fluorocytosine and the compound having formula (III) is between 1:5 to 5:1. In some embodiments, in the reaction of 5-fluorocytosine with the compound having formula (III), the molar ratio between 5-fluorocytosine and the compound having formula (III) is between 1:2 to 2:1. In some embodiments, in the reaction of 5-fluorocytosine with the compound having formula (III), the molar ratio between 5-fluorocytosine and the compound having formula (III) is between 1:1 to 1:2. In some embodiments, in the reaction of 5-fluorocytosine with the compound having formula (III), the molar ratio between 5-fluorocytosine and the compound having formula (III) is about 1:1. In some embodiments, in the reaction of 5-fluorocytosine with the compound having formula (III), the molar ratio between 5-fluorocytosine and the compound having formula (III) is about 1:1.1. In some embodiments, in the reaction of 5-fluorocytosine with the compound having formula (III), the molar ratio between 5-fluorocytosine and the compound having formula (III) is 1:1.2.

In some embodiments, in the reaction of 5-fluorocytosine with the compound having formula (III), the molar ratio between 5-fluorocytosine and the base is between 1:10 to 10:1. In some embodiments, in the reaction of 5-fluorocytosine with the compound having formula (III), the molar ratio between 5-fluorocytosine and the base is between 1:5 to 5:1. In some embodiments, in the reaction of 5-fluorocytosine with the compound having formula (III), the molar ratio between 5-fluorocytosine and the base is between 1:2 to 2:1. In some embodiments, in the reaction of 5-fluorocytosine with the compound having formula (III), the molar ratio between 5-fluorocytosine and the base is between 1:1 to 1:2. In some embodiments, in the reaction of 5-fluorocytosine with the compound having formula (III), the molar ratio between 5-fluorocytosine and the base is about 1:1. In some embodiments, in the reaction of 5-fluorocytosine with the compound having formula (III), the molar ratio between 5-fluorocytosine and the base is 1:1.2. In some embodiments, in the reaction of 5-fluorocytosine with the compound having formula (III), the molar ratio between 5-fluorocytosine and the base is 1:1.3.

In some embodiments, in the reaction of 5-fluorocytosine with the compound having formula (III), the molar ratio between the compound having formula (III) and the base is between 1:10 to 10:1. In some embodiments, in the reaction of 5-fluorocytosine with the compound having formula (III), the molar ratio between the compound having formula (III) and the base is between 1:5 to 5:1. In some embodiments, in the reaction of 5-fluorocytosine with the compound having formula (III), the molar ratio between the compound having formula (III) and the base is between 1:2 to 2:1. In some embodiments, in the reaction of 5-fluorocytosine with the compound having formula (III), the molar ratio between the compound having formula (III) and the base is between 1:1 to 1:2. In some embodiments, in the reaction of 5-fluorocytosine with the compound having formula (III), the molar ratio between the compound having formula (III) and the base is about 1:1. In some embodiments, in the reaction of 5-fluorocytosine with the compound having formula (III), the molar ratio between the compound having formula (III) and the base is 1:1.2.

In some embodiments, the reaction of 5-fluorocytosine with the compound having formula (III) to obtain the compound having formula (II) has a yield of at least 61%.

In some embodiments, the reaction of 5-fluorocytosine with the compound having formula (III) to obtain the compound having formula (II) has a yield higher than 60%, 70%, 80%, 90% or 99%. In some embodiments, the reaction of 5-fluorocytosine with the compound having formula (III) to obtain the compound having formula (II) has a yield higher than 90%.

In some embodiments, the impurities (A) and (B) in the invention process disclosed herein to obtain compound having the formula (II) is less than 20% based on the conversion. In some embodiments, the impurities (A) and (B) in the invention process disclosed herein to obtain compound having the formula (II) is less than 10% based on the conversion. In some embodiments, the impurities (A) and (B) in the invention process disclosed herein to obtain compound having the formula (II) is less than 5% based on the conversion. In some embodiments, the impurities (A) and (B) in the invention process disclosed herein to obtain compound having the formula (II) is less than 3% based on the conversion.

In some embodiments, the reaction of 5-fluorocytosine with the compound having formula (III) to obtain compound having the formula (II) further comprises a step of isolating the compound having formula (II) from the reaction mixture.

In some embodiments, isolation of the compound having formula (II) comprises (i) precipitation by adding a protic solvent to the reaction mixture, and (ii) filtration.

In some embodiments, the protic solvent is water, methanol or a combination thereof.

The present invention also provides a compound having formula (II) prepared using the process described herein.

The present invention also provides a compound having formula (IIai) prepared using the process described herein.

The compound having formula (II) may be alkylated to prepare the compound having formula (I) using the novel alkylation step described hereinbelow.

The compound having formula (II) may also be alkylated to prepare the compound having formula (I) using any suitable alkylation process known in the art including, but not limited to, the process described in PCT International Application Publication Nos. WO 2015/103142 and WO 2015/103144, the entire content of each of which is hereby incorporated by reference.

In some embodiments, the compound having formula (Iai) is prepared by contacting a compound having formula (IIai) with an alkali carbonate and an alkylating agent and forming a compound having formula (Iai).

In some embodiments, the contacting step is carried out between 22° C. and 60° C.

In some embodiments, the contacting step further includes a solvent selected from the group consisting of DMF, DMSO, DMA, NMP, and $CH_3CN$, and any combination thereof.

In some embodiments, the alkali carbonate is selected from the group consisting of $Na_2CO_2$, $K_2CO_3$, $Cs_2CO_3$, $Li_2CO_3$, and any combination thereof.

In some embodiments, the alkylating agent is selected from the group consisting of alkyl halides and benzyl halides. In some embodiments, the alkyl halide and benzyl halide are selected from the group consisting of methyl iodide ($CH_3I$), ethyl iodide ($C_2H_5I$), benzyl bromide (BnBr), and any combination thereof.

In some embodiments, the alkali carbonate base is $Cs_2CO_3$, and the solvent is DMF.

In some embodiments, a molar ratio of the compound having formula (IIai) to alkali carbonate base is from about 3:1 to about 1:1 and the molar ratio between the compound having formula (IIai) to alkylating agent is from about 1:1 to about 1:3. In some embodiments, the molar ratio of the compound having formula (IIai) to alkali carbonate base is about 2:1 and the molar ratio of the compound having formula (IIai) to alkylating agent is 1:3.

In some embodiments, the process further includes the step of diluting a completed reaction mixture with $CH_3CN$ and 2.5% aqueous $Na_2S_2O_3$. In some embodiments, the ratio of DMF to $CH_3CN$ is from about 1:1 to about 3:1 and the ratio of DMF to 2.5% aqueous $Na_2S_2O_3$ is from about 1:2 to about 2:1. In some embodiments, the ratio of DMF to $CH_3CN$ is about 2:1 and the ratio of DMF to 2.5% aqueous $Na_2S_2O_3$ is about 1:1.

In some embodiments, the compound having formula (Iai) is prepared by contacting a compound having formula (IIai) with an alkali alkoxide and an alkylating agent and forming a compound having formula (Iai).

In some embodiments, the contacting step is carried out between 22° C. and 60° C.

In some embodiments, the contacting step further includes a solvent selected from the group consisting of DMF, DMSO, DMA, NMP, $CH_3CN$, and any combination thereof.

In some embodiments, the alkali alkoxide is selected from the group consisting of KOtBu, $CH_3ONa$, $CH_3CH_2ONa$, $CH_3CH_2OLi$, $CH_3OLi$, $CH_3CH_2OK$, $CH_3CH_2Ona$, and any combination thereof.

In some embodiments, the alkylating agent is selected from the group consisting of alkyl halides and benzyl halides.

In some embodiments, the alkyl halide and benzyl halide are selected from the group consisting of methyl iodide ($CH_3I$), ethyl iodide ($C_2H_5I$), benzyl bromide (BnBr), and any combination thereof.

In some embodiments, the alkali alkoxide is KOtBu, and the solvent is DMF.

In some embodiments, the molar ratio of the compound having formula (IIai) to alkali alkoxide is from about 3:1 to about 1:1 and the molar ratio of the compound having formula (IIai) to alkylating agent is from about 1:1 to about 1:3. In some embodiments, the molar ratio of the compound having formula (Thai) to alkali alkoxide base is about 2:1 and the molar ratio of the compound having formula (IIai) to alkylating agent is 1:3.

In some embodiments, the process includes diluting a completed reaction mixture with $CH_3CN$ and 2.5% aqueous $Na_2S_2O_3$. In some embodiments, the ratio of DMF to $CH_3CN$ is from about 1:1 to about 3:1 and the ratio of DMF to 2.5% aqueous $Na_2S_2O_3$ is from about 1:2 to about 2:1. In some embodiments, the ratio of DMF to $CH_3CN$ is about 2:1 and a ratio of DMF to 2.5% aqueous $Na_2S_2O_3$ is about 1:1.

In some embodiments, the compound having formula (Iai) is prepared by contacting a compound having formula (IIai) with a base, such as an alkali carbonate, e.g., sodium-, potassium-, cesium-, and lithium carbonate ($Na_2CO_3$, $K_2CO_3$, $Cs_2CO_3$, and $Li_2CO_3$, respectively) or an alkali alkoxide, for example, potassium tert-butoxide (KOtBu) and an alkylating agent, such as an alkyl halide of formula $CH_3$—X, wherein X is a halogen, e.g., iodine, bromine, and chlorine, in a polar solvent, such as N,N-dimethylformamide (DMF), dimethylsulfoxide (DMSO), dimethylacetamide (DMA), N-methylpyrrolidone (NMP), acetonitrile ($CH_3CN$), and the like, at concentrations from about 0.1 molar (M) to about 3 M. In some embodiments, the reactions are conducted at temperatures between −78° C. and 90° C. In some embodiments, the reactions are conducted between 22° C. and 60° C.

Reacting the Compound Having Formula (II) to Obtain the Compound Having Formula (I) (the Alkylation Step)

Reacting the compound having formula (II) to obtain the compound having formula (I) is challenging.

In some embodiments, the reaction of the compound having formula (II) with DMS is conducted in the absence of base.

In some embodiments, the reaction of the compound having formula (II) with DMS is conducted in the presence of at least one base.

In some embodiments, the base is selected from the group consisting of DABCO, TBAB, NaOH, $K_2CO_3$, $KHCO_3$, $Na_2CO_3$, $Et_3N$, NaOMe, NaOEt and any combination thereof.

In some embodiments, the base is selected from the group consisting of TBAB, NaOH, $Na_2CO_3$, $Et_3N$, NaOMe, and any combination thereof.

In some embodiments, the reaction of the compound having formula (II) with DMS is conducted at a temperature between 25-85° C. In some embodiments, the temperature is between 25-50° C. In some embodiments, the reaction of the compound having formula (II) with DMS is conducted at a temperature between 35-50° C.

In some embodiments, the molar ratio between the compound having formula (II) and DMS is between 1:2 to 1:10. In some embodiments, the molar ratio between the compound having formula (II) and DMS is between 1:2 to 1:5. In some embodiments, the molar ratio between the compound having formula (II) and DMS is between 1:2 to 1:4. In some embodiments, the molar ratio between the compound having formula (II) and DMS is about 1:3. In some embodiments, the molar ratio between the compound having formula (II) and DMS is about 1:3.5.

In some embodiments, the molar ratio between the compound having formula (II) and the base is 1:0.1 to 1:10. In some embodiments, the molar ratio between the compound having formula (II) and the base is 1:0.1 to 1:5.5.

In some embodiments, the base is added after 4 hours from the beginning of the reaction of compound (II) with DMS. Suitable bases include alkoxides and carbonates.

In some embodiments, the base is added after 4 hours from the beginning of the reaction of the compound having formula (II) with DMS and the temperature of the reaction is above 30 degrees Celsius.

In some embodiments, the base is added at the beginning of the reaction. Suitable bases include DABCO, $NEt_3$, $LiCO_3$, and $KHCO_3$.

When the base is added at the beginning of the reaction of the compound having formula (II) with DMS, the temperature is preferably above 30 degrees Celsius.

In some embodiments, the reaction of the compound having formula (II) with DMS is conducted in the presence of at least one solvent. In some embodiments, the reaction of the compound having formula (II) with DMS is conducted in the presence of two solvents.

In some embodiments, the solvent is a polar solvent.

In some embodiments, the polar solvent has a dielectric constant equal to or above 5. In some embodiments, the polar solvent has a dielectric constant equal to or above 10. In some embodiments, the polar solvent has a dielectric constant equal to or above 15. In some embodiments, the polar solvent has a dielectric constant equal to or above 20.

In some embodiments, the solvent is selected from the group consisting of DMA, CPME, MeTHF, DMA, DMF, DCM and any combination thereof.

In some embodiments, the solvent is DMA. In some embodiments, the solvent is CPME. In some embodiments, the solvent is MeTHF.

In some embodiments, the solvent is MeTHF and the base is $NEt_3$.

In some embodiments, the solvent is a mixture of at least two solvents.

In some embodiments, the solvent is a mixture of DMA and CPME.

In some embodiments, the weight ratio between DMA and CPME is between 1:1 to 1:10. In some embodiments, the weight ratio between DMA and CPME is between 1:1 to 1:4. In some embodiments, the weight ratio between DMA and CPME is between 1:2 to 1:4. In some embodiments, the weight ratio between DMA and CPME is between 1:3 to 1:5. In some embodiments, the weight ratio between DMA and CPME is about 1:4.

In some embodiments, the solvent is a mixture of DMA and MeTHF.

In some embodiments, the solvent is a mixture of DMA and MeTHF in a weight ratio of 1:1 to 1:4. In some embodiments, the solvent is a mixture of DMA and MeTHF in a weight ratio of 1:2 to 1:4.

In some embodiments, the alkylation process is conducted in the presence of a mixture of DMA and CPME in a weight ratio of 1:2 to 1:4. In some embodiments, the alkylation process is conducted in the presence of a mixture of DMA and CPME in a weight ratio of 1:4.

In some embodiments, in the reaction of the compound having formula (II) with DMS, the molar ratio between the solvent or mixture of solvents to the compound having formula (II) is between 30:1 and 1:1. In some embodiments, in the reaction of the compound having formula (II) with DMS, the molar ratio between the solvent or mixture of solvents to the compound having formula (II) is between 20:1 and 5:1. In some embodiments, in the reaction of the compound having formula (II) with DMS, the molar ratio between the solvent or mixture of solvents to the compound having formula (II) is between 15:1 and 10:1. In some embodiments, in the reaction of the compound having formula (II) with DMS, the molar ratio between the solvent or mixture of solvents to the compound having formula (II) is between 14:1 to 12:1. In some embodiments, in the reaction of the compound having formula (II) with DMS, the molar ratio between the solvent or mixture of solvents to the compound having formula (II) is about 13:1. In some embodiments, in the reaction of the compound having formula (II) with DMS, the molar ratio between the solvent or mixture of solvents to the compound having formula (II) is 12.7:1.

In some embodiments, in the reaction of the compound having formula (II) with DMS, the molar ratio between the solvent or mixture of solvents to DMS is between 10:1 to 1:1. In some embodiments, in the reaction of the compound having formula (II) with DMS, the molar ratio between the solvent or mixture of solvents to DMS is between 5:1 to 3:1. In some embodiments, in the reaction of the compound having formula (II) with DMS, the molar ratio between the solvent or mixture of solvents to DMS is about 4:1. In some embodiments, in the reaction of the compound having formula (II) with DMS, the molar ratio between the solvent or mixture of solvents to DMS is 3.9:1.

In some embodiments, the reaction of the compound having formula (II) with DMS further comprises neutralizing with an aqueous basic solution.

In some embodiments, the excess DMS is neutralized with an aqueous basic solution.

In some embodiments, the weight ratio of the DMA:CPME:compound having the formula (II) is 1.5:0:1 to 1:5:1.

In some embodiments, the process for preparing the compound 5-fluoro-4-imino-3-methyl-1-(toluene-4-sulfonyl)-3,4-dihydro-1H-pyrimidin-2-one, the compound having formula (I), from the compound having formula (II) further comprises an isolation step.

In some embodiments, the process for preparing the compound 5-fluoro-4-imino-3-methyl-1-(toluene-4-sulfonyl)-3,4-dihydro-1H-pyrimidin-2-one, the compound having formula (I), from the compound having formula (II)

further comprises an additional step of adding an aqueous basic solution to the reaction mixture.

In some embodiments, the process for preparing the compound 5-fluoro-4-imino-3-methyl-1-(phenyl-4-sulfonyl)-3,4-dihydro-1H-pyrimidin-2-one, the compound having formula (I), from the compound having formula (II) further comprises an isolation step.

In some embodiments, the process for preparing the compound 5-fluoro-4-imino-3-methyl-1-(phenyl-4-sulfonyl)-3,4-dihydro-1H-pyrimidin-2-one, the compound having formula (I), from the compound having formula (II) further comprises isolating the compound having formula (I) from the reaction mixture.

In some embodiments, the process for preparing the compound 5-fluoro-4-imino-3-methyl-1-(phenyl-4-sulfonyl)-3,4-dihydro-1H-pyrimidin-2-one, the compound having formula (I), from the compound having formula (II) further comprises an additional step of adding an aqueous basic solution.

In some embodiments, the base in the aqueous basic solution may include but is not limited to $K_2CO_3$, $KHCO_3$, $Na_2CO_3$, $NaHCO_3$, $K_2CO_3$ $NH_4OH$, NaOH or any combination thereof. In some embodiments, the concentration of the base in the aqueous basic solution is 2-15% based on the total weight (w/w).

In some embodiments, the base in the aqueous basic solution is $K_2CO_3$.

In some embodiments, the step of adding an aqueous basic solution comprises additional use of a phase transfer catalyst (PTC) such as tetra-n-butylammonium bromide (TBAB).

In some embodiments, the reaction of the compound having formula (II) with DMS to obtain the compound having formula (I) has a yield of at least 60%. In some embodiments, the reaction of the compound having formula (II) with DMS to obtain the compound having formula (I) has a yield of at least 70%. In some embodiments, the reaction of the compound having formula (II) with DMS to obtain the compound having formula (I) has a yield of at least 80%.

The compound having formula (II) may be prepared using the sulfonation process described herein.

The compound having formula (II) may also be prepared using any process known in the art including, but not limited to, the process described in POT International Application Publication Nos. WO 2015/103142 and WO 2015/103144, the entire content of each of which is hereby incorporated by reference.

In some embodiments, the compound having formula (IIai) is prepared by contacting a compound having formula (IV):

IV

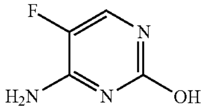

with bis-N,O-trimethylsilylacetamide (BSA) and forming a compound having formula (IIai), wherein the molar ratio of the compound having formula (IV) to bis-N,O-trimethylsilylacetamide (BSA) is 1:1.1 and the contacting step is carried out at a temperature from about 22° C. to about 70° C.

In some embodiments, the contacting step further includes contacting the compound having formula (IV) with $CH_3CN$.

In some embodiment, the process comprises contacting a BSA treated reaction mixture with an arylsulfonyl chloride.

In some embodiments, the molar ratio between the compound having formula (IV) to arylsulfonyl chloride is from about 1:2 to about 2:1. In some embodiments, the molar ratio between the compound having formula (IV) to arylsulfonyl chloride 1:1.1.

In some embodiments, the compound having formula (IIai) may be prepared by contacting a compound having formula (IV) with bis-N,O-trimethylsilylacetamide (BSA) at an elevated temperature, such as 70° C., for a period of about 1 hour (h), followed by cooling and contacting the solution containing the protected pyrimidinol with $CH_3$-$PhSO_2Cl$ at about 20° C.-25° C. In some embodiments, the molar ratio between the compound having formula (IV) to BSA and the sulfonyl chloride is about 1:3:1.1, respectively. In some embodiments, reducing the molar ratio of the reactants to about 1:1.1:1.1 affords improved yields.

Isolation of Compound Having the Formula (I), Route 1

The present invention provides a method for isolating a compound having formula (I) from a mixture thereof, the method comprising contacting the mixture comprising the compound having formula (I) with a solvent or a mixture of solvents and filtering the precipitated solid.

In some embodiments, the mixture comprises the compound having formula (I) and DMS. In some embodiments, the process comprises contacting the mixture comprising the compound having formula (I) and DMS with a solvent or a mixture of solvents and filtering the precipitated solid.

In some embodiments, the solvent is polar. In some embodiments, the solvents are polar.

In some embodiments, the polar solvent has a dielectric constant equal to or above 5. In some embodiments, the polar solvent has a dielectric constant equal to or above 10. In some embodiments, the polar solvent has a dielectric constant equal to or above 15. In some embodiments, the polar solvent has a dielectric constant equal to or above 20.

In some embodiments, the polar solvent is an organic polar solvent.

In some embodiments, the solvent is selected from the group consisting of DMA, CPME, MeTHF, DMA, DMF, DCM and any combination thereof.

In some embodiments, the polar solvent is DMA. In some embodiments, the polar solvent is CPME. In some embodiments, the polar solvent is MeTHF.

In some embodiments, the method comprises evaporation of the polar solvent prior to filtration. In some embodiments, the method comprises partial evaporation of the polar solvent prior to filtration.

In some embodiments, the method comprises cooling the reaction mixture prior to filtration.

The method for isolating a compound having formula (I) from a mixture thereof may be used to isolate a compound having formula (I) from any mixture thereof, including, but not limited to, (i) the reaction mixture after preparing the compound having formula (I) using the processes described herein, (ii) the reaction mixture after preparing the compound having formula (I) using the processes described in PCT International Application Publication Nos. WO2015/103144 and WO2015/103142, and (iii) the reaction mixture after preparing the compound having formula (I) using the processes described in PCT International Application No. PCT/IB2020/058893. The entire content of each of WO2015/103144, WO2015/103142, and PCT/IB2020/058893 is hereby incorporated by reference.

Isolation of Compound Having the Formula (I), Route 2

The present invention provides a method for isolating compound having the formula (I) comprising (1) washing of an organic solution comprising a polar water immiscible solvent and a mixture of compound (I) and DMS with 2-15% w/w of aqueous basic solution, (2) separating the organic phase from the water phase, and (3) concentrating the organic phase and filtering the precipitated solid.

The present invention provides a method for isolating the compound having the formula (I) from a mixture comprising the compound having formula (I) and DMS, wherein the method comprises (1) dissolving the mixture comprising the compound having formula (I) and DMS in an organic polar solvent to obtain an organic solution, (2) washing the organic solution obtained from (1) with 2-15% w/w of aqueous basic solution, (3) separating the organic phase from the water phase, and (4) concentrating the organic phase and filtering the precipitated solid.

In some embodiments, the polar solvent has a dielectric constant equal to or above 5. In some embodiments, the polar solvent has a dielectric constant equal to or above 10. In some embodiments, the polar solvent has a dielectric constant equal to or above 15. In some embodiments, the polar solvent has a dielectric constant equal to or above 20.

In some embodiments, the organic polar solvent is an organic polar water immiscible solvent.

In some embodiments, the organic water immiscible solvent has a dielectric constant less than 20.

In some embodiments, organic water immiscible solvent includes but is not limited to methyl tetrahydrofuran (MeTHF), cyclopentylmethylether (CPME), and a mixture thereof.

In some embodiments, the organic polar solvent is selected from the group consisting of DMA, CPME, MeTHF, DMA, DMF, DCM and any combination thereof.

In some embodiments, the organic polar solvent is DMA. In some embodiments, the organic polar solvent is CPME. In some embodiments, the organic polar solvent is MeTHF.

In some embodiments, the aqueous basic solution is an aqueous solution of a base selected from the group consisting of DABCO, TBAB, NaOH, $K_2CO_3$, $KHCO_3$, $Na_2CO_3$, $Et_3N$, NaOMe, NaOEt and any combination thereof.

In some embodiments, the aqueous basic solution is an aqueous solution of $K_2CO_3$.

In some embodiments, the compound having formula (I) is a compound having formula (Ia) wherein R is alkyl.

In some embodiments, the compound having formula (Ia) is a compound having formula (Iai) wherein R is methyl.

In some embodiments, the organic phase is cooled prior to and/or during the filtration. In some embodiments, the organic phase is cooled to 0-5° C.

In some embodiments, the organic polar solvent is added after the reaction to obtain the compound having the formula (I). In some embodiments, the CPME is added after the reaction to obtain the compound having the formula (I).

In some embodiments, a partial amount of the organic polar solvent is present from the reaction to obtain the compound having formula (I) and optionally additional amount of the organic polar solvent is added before isolation of the compound having formula (I). In some embodiments, a partial amount of the CPME is present from the reaction to obtain the compound having formula (I) and optionally an additional amount of CPME is added before isolation of the compound having formula (I).

Isolation of Compound Having the Formula (I), Route 3

The present invention provides a method for isolating the compound having formula (I) from a mixture comprising the compound having formula (I) and DMS, wherein the method comprises (1) mixing the mixture comprising (i) the compound having formula (I), (ii) DMS and optionally (iii) a solvent with 2-15% w/w of an aqueous basic solution to obtain slurry mixture containing solids, and (2) filtering the precipitated solids.

In some embodiments, the mixture comprises a solvent.

In some embodiments, the slurry mixture comprises a solvent.

In some embodiments, the solvent is the same as the solvent used in obtaining the compound having formula (I).

In some embodiments, the solvent is a polar solvent.

In some embodiments, the polar solvent has a dielectric constant equal to or above 5. In some embodiments, the polar solvent has a dielectric constant equal to or above 10. In some embodiments, the polar solvent has a dielectric constant equal to or above 15. In some embodiments, the polar solvent has a dielectric constant equal to or above 20.

In some embodiments, the slurry mixture is mixed for 30 minutes to 8 hours.

In some embodiments, the slurry mixture is mixed at temperature between 25 to 60 degrees Celsius.

In some embodiments, the slurry mixture is mixed using mechanical stirrer.

In some embodiments, the slurry mixture is mixed using high shear stirrer.

In some embodiments, the slurry mixture is mixed using both mechanical stirrer and high shear stirrer.

In some embodiments, the slurry mixture is obtained by adding the mixture comprising the compound having formula (I) and DMS and optionally organic solvent into a 2-15% of aqueous basic solution.

In some embodiments, the slurry mixture obtained by adding the 2-15% aqueous basic solution into a mixture comprising the compound having formula (I), DMS and optionally an organic solvent.

In some embodiments, the filtered solid obtained in step (2) is washed with an organic solvent during filtration in step (2). In some embodiments, the organic solvent is CPME.

In some embodiments, the filtered solid obtained in step (2) is washed with water during filtration in step (2).

In some embodiments, the filtered solid is mixed with water and stirred for 1 to 3 hours and filtered.

In some embodiments, the stirring the filtered with water the filtered solid is mixed with water is conducted at temperature of 25-40 degrees Celsius and filtered.

In some embodiments, the organic solvent is the same organic solvent as used in obtaining the compound having formula (I).

In some embodiments, the aqueous basic solution is 10% of $K_2CO_3$ in water based on the total weight (w/w) of $K_2CO_3$ in water.

In some embodiments, the organic phase is the solution which is obtained in the reaction of compound having the formula (II) with DMS.

In some embodiments, the organic phase is obtained by adding an organic water immiscible solvent to the mixture of the compound having formula (I) and DMS obtained in the reaction of compound (II) and DMS.

In some embodiments, the step of adding an aqueous basic solution comprises additional use of a phase transfer catalyst (PTC) such as tetra-n-butylammonium bromide (TBAB).

In some embodiments, a solution of the compound having formula (I) in CPME is obtained by mixing CPME and the compound having formula (I) in weight ratio of 10:1 prior to washing with 2-15% w/w of aqueous basic solution.

In some embodiments, the solution of the compound having formula (I) in CPME is obtained by warming the combination of CPME and the compound having formula (I) up to 65° C. prior to washing with 2-15% w/w of aqueous basic solution.

In some embodiments, the solution of the compound having formula (I) in CPME is obtained by warming the combination of CPME and the compound having formula (I) up to about 50° C. prior to washing with 2-15% w/w of aqueous basic solution. In some embodiments, the resultant mixture obtained from the reaction of the compound having formula (II) with DMS is dissolved in CPME.

In some embodiments, the resultant mixture obtained from the reaction of the compound having formula (II) with DMS is dissolved with CPME and washed with water base solution.

In some embodiment the resultant mixture is a mixture of the compound having formula (I) with the solvent which was used in the reaction of the compound having formula (II) with DMS.

In some embodiments, the conversion of the 5-fluoro-4-imino-1-(toluene-4-sulfonyl)-3,4-dihydro-1H-pyrimidin-2-one to 5-fluoro-4-imino-3-methyl-1-(toluene-4-sulfonyl)-3,4-dihydro-1H-pyrimidin-2-one is higher than 50%.

In some embodiments, the chemical yield of 5-fluoro-4-imino methyl-1-(toluene-4-sulfonyl)-3,4-dihydro-1H-pyrimidin-2-one is higher than 50%. The yield of the purified 5-fluoro-4-imino methyl-1-(toluene-4-sulfonyl)-3,4-dihydro-1H-pyrimidin-2-one is higher than 50%, 50%, 70%, 80%, 90% or 99%.

In some embodiments, the conversion of the 5-fluoro-4-imino-1-(toluene-4-sulfonyl)-3,4-dihydro-1H-pyrimidin-2-one to 5-fluoro-4-imino-3-methyl-1-(phenyl-4-sulfonyl)-3,4-dihydro-1H-pyrimidin-2-one is higher than 50%.

In some embodiments, the chemical yield of 5-fluoro-4-imino-3-methyl-1-(phenyl-4-sulfonyl)-3,4-dihydro-1H-pyrimidin-2-one is higher than 50%. The yield of the purified 5-fluoro-4-imino-3-methyl-1-(toluene-4-sulfonyl)-3,4-dihydro-1H-pyrimidin-2-one is higher than 50%, 50%, 70%, 80%, 90% or 99%.

The present invention also provides a compound having formula (I) prepared using the process described herein.

The present invention also provides a compound having formula (Iai) prepared using the process described herein.

The present reactions occur under reaction conditions sufficient to produce the desired compound. Such conditions, e.g. temperature, time, molarity, etc., may be varied by one of ordinary skill in the art based on the methods and protocols described herein.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

The invention is illustrated by the following examples without limiting it thereby.

EXAMPLES

Examples of the Sulfonation Step

Example 1: Reacting 5-Fluorocytosine with Compound Having the Formula (III) in DMA and Water and $K_2CO_3$ as Base 5-fluorocytosine (99%, 80.1 gr) was added to 1 L glass reactor that contains 200 gr of water and 200 gr of DMA. $K_2CO_3$ (solid, 114.9 gr, 1.35 mol equiv.) was added and the reactor was cooled to 0° C. Tosyl chloride (128 gr, 1.05 mol equiv.) was added in one portion at 0° C. and the solution was mixed at temperature of 0° C. to 5° C. The reaction was monitored using HPLC and then 200 gr of water were added and the temperature was heated to 25° C. and mixed for 2 hours. The obtained solid was filtered off using Buchner funnel. The cake was washed with water and dried in vacuum oven at 55 to 65° C. 178 gr of desired product were obtained in purity of 90.9% and yield of 93%.

The product contains impurity A (2.4%) and impurity B (0.2%).

Example 2: Reacting 5-Fluorocytosine with Compound Having the Formula (III) in DMA and $Et_3N$ as Base To 40 gr of 99.2% 5-fluorocytosine in 120 gr of DMA, 34.2 gr of $Et_3N$ was added. The mixture cooled down to 0° C. 1.05 eq of TSCl was added, and the reaction mixture was stirred for 4 hours at 3° C. The reaction was monitored using HPLC. The conversion towards the product was 94.5%.

250 gr of water was added to the mixture and heated to 15° C. The solid was filtered off and dried in vacuum oven to obtain the desired product at 75% isolated yield. Chemical yield-77%. The product was obtained in 78.8% purity and contains impurity B (1%).

Example 3: Reacting 5-Fluorocytosine with Compound Having the Formula (III) in DMA and Water and $K_2CO_3$ as Base To 5 gr of 99.2% 5-fluorocytosine in 20 gr of water and 10 gr of DMA, 8.5 gr of $K_2CO_3$ (1.6 eq) was added. The reaction mixture was cooled down to 5° C., and 8.4 gr of TSCl (1.1 eq) was added. The reaction mixture was stirred for 3 hours at 5° C. HPLC monitoring detected 92% of the desired product. The precipitate was filtered off and dried in vacuum oven at 55° C. for 12 hours to yield the product as white solid with purity of 84% and isolated yield of 85%. The product contains impurity A (6%).

Example 4(a): Reacting 5-Fluorocytosine with Compound Having the Formula (III) in ACN and $Et_3N$ as Base To 30 gr of 99.2% 5-fluorocytosine in 165 gr of ACN, 30.4 gr of $Et_3N$ (1.3 eq) was added. The mixture was cooled down to 0° C. Afterwards, 50.6 gr of TSCl (1.15 eq) was added in two portions at 0° C. The reaction mixture was stirred for 4 hours. The reaction was monitored using HPLC. 310 gr of water was added to the mixture, heated to 10° C., and stirred for 1 hour. The solid was filtered off and dried in vacuum oven to obtain the desired product at 54% isolated yield. Chemical yield was 63%. The product was obtained in purity of 68.8% and contains impurity B (6.1%) and impurity A (0.7%).

Example 4(b): Reacting 5-Fluorocytosine with Compound Having the Formula (III) in ACN and $Et_3N$ as Base To 5 gr of 99.2% 5-fluorocytosine in 15 gr of ACN, 4.7 gr of $Et_3N$ was added. The mixture was cooled down to 5° C. Afterwards, 8.1 gr of TSCl was added, and the reaction mixture was stirred for 2 hours at 5° C. The reaction was monitored using HPLC. MeOH was added to the mixture and the solid was filtered off and dried in vacuum oven to obtain the desired product at 60.8% isolated yield. Chemical yield=74%. The product was obtained in purity of 73.7% and contains impurity B (0.3%) and impurity A (0.5%).

Example 4(c): Reacting 5-Fluorocytosine with Compound Having the Formula (III) in MeCN and $NEt_3$ 5-fluorocytosine (99%, 5 gr) was added to a round bottom flask that contained 15 gr of acetonitrile. Triethylamine (4.6 gr, 1.2 mol equiv.) was added and the flask was cooled to 5° C. Tosyl chloride (8 gr, 1.1 mol equiv.) was added in one portion at 5° C. and the solution was mixed at a temperature of 5° C. The reaction was monitored using HPLC and then methanol was added and the temperature was heated to 25° C. and mixed for 2 hours. The obtained solid was filtered off using Buchner funnel. 9 gr of desired product was obtained in purity of 74% and yield of 61%. The product contains impurity A (0.5%) and impurity B (0.3%).

Example 5: Reacting 5-Fluorocytosine with Compound Having the Formula (III) in Water and DMA and DMAP as Base To 5 gr of 99.2% of 5-fluorocytosine in 15 gr of water and 10 gr of DMA, 1.4 gr of DMAP was added. The reaction mixture was cooled down to 5° C., and 9.15 gr of TSCl was added. The reaction pH was adjusted to 9-10, using 20% of NaOH solution. After reaching 86% of the product in HPLC, the reaction mixture was heated to 25° C. The precipitate was filtered off, washed with water and dried in vacuum oven to yield the desired product in isolated yield of 59%.

The product was obtained in purity of 79.6% and contains impurity B (0.75%) and impurity A (0.32%).

Example 6: Reacting 5-Fluorocytosine with Compound Having the Formula (III) in MeCN and Triethylamine as Base To 30 gr of 99.2% 5-fluorocytosine in 165 gr of ACN, 30.4 gr of $Et_3N$ (1.3 eq) was added. The mixture was cooled down to 0° C. Afterwards, 50.6 gr of TSCl (1.15 eq) was added in two portions at 0° C. The reaction mixture was stirred for 4 hours. The reaction was monitored using HPLC. 310 gr of water was added to the mixture, heated to 10° C., and stirred for 1 hour. The solid was filtered off and dried in vacuum oven to obtain the desired product at 54% isolated yield. Chemical yield was 63%. The product was obtained in purity of 68.8% and contains impurity B (6.1) and impurity A (0.7%).

Example 7: Reacting 5-Fluorocytosine with Compound Having the Formula (III) in MeCN and Triethylamine as Base To 5 gr of 99.2% 5-fluorocytosine in 15 gr of MeCN, 4.7 gr of $Et_3N$ was added. The mixture was cooled down to 5° C. Afterwards, 8.1 gr of TSCl was added, and the reaction mixture was stirred for 2 hours at 5° C. The reaction was monitored using HPLC. MeOH was added to the mixture and the solid was filtered off and dried in vacuum oven to obtain the desired product at 60.8% isolated yield. Chemical yield=74%. The product was obtained in purity of 73.7% and contains impurity B (0.3) and impurity A (0.5%).

Example 8: Reacting 5-Fluorocytosine with Compound Having the Formula (III) in DMA and Sodium Carbonate as Base To 5 gr of 99.2% 5-fluorocytosine in 35 gr of DMA, 6.38 gr of $Na_2CO_3$ is added. The mixture is cooled down to 5° C. Afterwards, 8.37 gr of TSCl is added, and the reaction mixture is stirred for 3 hr at 5° C. The reaction is sampled in HPLC. Partial conversion of starting material is obtained. The product is not isolated.

Example 9: Reacting 5-Fluorocytosine with Compound Having the Formula (III) in DMBA and Sodium Carbonate as Base To 5 gr of 99.2% 5-fluorocytosine in 35 gr of DMBA, 6.38 gr of $Na_2CO_3$ is added. The mixture is cooled down to 5° C. Afterwards, 8.37 gr of TSCl is added, and the reaction mixture is stirred for 3 hr at 5° C. The reaction is sampled in HPLC. Partial conversion of starting material is obtained. The product is not isolated.

Example 10: Reacting 5-Fluorocytosine with Compound Having the Formula (III) in Water and DMAP as Base To 5 gr of 99.2% 5-fluorocytosine in 40 gr of water, 2.35 gr of 4-DMAP was added. 8.8 gr of TSCl was added, and the reaction mixture stirred for 4 hr at 25° C. The reaction was sampled in HPLC. 50% of desired product was obtained. The conversion of starting material was 51%. The product was not isolated.

Example 11: Reacting 5-Fluorocytosine with Compound Having the Formula (III) in DMA, Water and DMBA and Potassium Hydroxide as Base To 5 gr of 99.2% 5-fluorocytosine in 15 gr of DMA, 15 gr of water and 1.56 gr of N,N-dimethylbenzylamine are added. The mixture is cooled down to 5° C. Afterwards, 9.13 gr of TSCl is added, and the reaction mixture is stirred for 4 hr at 5° C. while keeping pH at 9-10 using potassium hydroxide 20% in water. The reaction is sampled in HPLC. The product is obtained in partial selectivity and is not isolated.

Example 12: Reacting 5-Fluorocytosine with Compound Having the Formula (III) in DMA, Water and DMBA and Sodium Hydroxide as Base To 5 gr of 99.2% 5-fluorocytosine in 15 gr of DMA, 15 gr of water and 1.56 gr of N,N-dimethylbenzylamine was added. The mixture was cooled down to 5° C. Afterwards, 9.13 gr of TSCl was added, and the reaction mixture was stirred for 4 hr at 5° C. while keeping pH at 9-10 using sodium hydroxide 20% in water. The reaction was sampled in HPLC. 78.3% of desired product was obtained, in conversion of 82%. 3.8% of product isomer was obtained. The product was not isolated.

Example 13: Reacting 5-Fluorocytosine with Compound Having the Formula (III) in DMA and Water and $K_2CO_3$ as Base 5-fluorocytosine (99%, 120 gr) was added to 1 L glass reactor that contains 360 gr water and 160 gr of DMA. $K_2CO_3$ (204 gr, 1.6 mol equiv.) was added and the reactor was cooled to −5° C. Tosyl chloride (192 gr, 1.05 mol equiv.) was added in one portion at −5° C. to −3° C. over 1.5 hours and the solution was mixed at temperature of −5° C. for 3.5 hours. The reaction was monitored using HPLC. 93% selectivity was observed. The reaction was heated to 15° C. and the product was filtered off and dried in vacuum oven at 55° C. 329 gr of product in purity of 60% was obtained. The isolated yield was 76%.

Examples of the Alkylation Step

Example 14: Reaction of Compound Having the Formula (IIai) with Dimethylsulphate (DMS) in Absence of Base in CPME and DMA 4800 gr CPME, 1200 gr DMA and 1700 gr 5-fluoro-4-imino-1-(toluene-4-sulfonyl)-3,4-dihydro-1H-pyrimidin-2-one (IIai) (81% purity) were added into a 25 L reactor. The mixture was heated to 35° C. and dimethylsulfate was added (2000 gr, 3.5 mol equiv.) over 30 minutes. The reaction was stirred for 4 hours at 35-40° C. 9000 gr CPME was added and the mixture was heated to 50° C. until a clear solution was obtained. An aqueous solution of $ItCO_3$ (10% w, 10 kg) was added and the mixture was stirred for 30 minutes. The phases were separated and the organic phase was mixed with another 5 kg solution of 10% $K_2CO_3$ containing 85 gr of TBAB for 1 hour followed by phase separation and repeating the same procedure again. The organic phase was washed with 9 kg of water and then 10 kg of CPME was evaporated at 100 mbar at 50° C.

The solution was cooled to 0-5° C. and the obtained solid was filtered off using Buchner funnel. The cake was washed with 1 liter of cold water and dried in vacuum oven at 65° C. 1222 gr of product was obtained in 98.9% purity and 80% isolated yield.

Example 15(a): Reaction of Compound Having the Formula (IIai) with Dimethylsulphate (DMS) in CPME and DMA and in the Presence of TBAB To a mixture of 40 gr of 5-fluoro-4-imino-1-(toluene-4-sulfonyl)-3,4-dihydro-1H-pyrimidin-2-one (IIai) at purity of 86.8%, 200 gr of CPME, 50 gr of DMA, TBAB 5%, and 3 eq of dimethylsulfate was added as one portion. The reaction mixture was heated to 40° C. for 6 hours. Then, 250 gr of CPME was added, and the reaction mixture heated to 50° C. and washed twice with 300 gr of 10% $K_2CO_3$ solution. The last wash was with 300 gr of water at 50° C. The organic phase was concentrated under reduced pressure and the residues cooled down to 5° C., the formed solid was filtered off, washed with CPME and dried in vacuum oven at 65° C. to obtain the desired product at 94.5% purity, and isolated yield of 80.4%.

Example 15(b): Reaction of Compound Having the Formula (IIai) with Dimethylsulphate (DMS) in DMA and in the Presence of NaOMe To a mixture of 5 gr 5-fluoro-4-imino-1-(toluene-4-sulfonyl)-3,4-dihydro-1H-pyrimidin-2-one (IIai) at purity of 85.3%, 15 gr of DMA, 0.2 eq of NaOMe, 4 eq of dimethylsulfate was added. The reaction mixture was heated to 35° C. for 5 hours. 45 gr of CPME was added, and heated to 50° C. The organic phase was washed twice using 10% $K_2CO_3$ solution, and washed a third time with 50 gr of water. The phase separation was performed at 50° C. The organic phase was concentrated under vacuum to yield the desired product at 51% isolated yield.

Example 16: Reaction of Compound Having the Formula (IIai) with dimethylsulphate (DMS) in absence of base in CPME and DMA 1:1

2000 gr CPME, 2000 gr DMA and 2000 gr 5-fluoro-4-imino-1-(toluene-4-sulfonyl)-3,4-dihydro-1H-pyrimidin-2-one (Thai) (81% purity) were added into a 25 L reactor. The mixture was heated to 35° C. and dimethylsulfate was added (2200 gr, 3 mol equiv.) over 60 minutes. The reaction was stirred for 4 hours at 35-40° C. 14000 gr CPME was added and the mixture was heated to 50° C. until a clear solution was obtained. An aqueous solution of $K_2CO_3$ (15% w, 11.5 kg) was added and the mixture was stirred for 60 minutes at 60° C. The phases were separated and the organic phase was mixed with another 6 kg solution of 10% $K_2CO_3$ for 0.5 hour followed by phase separation. The organic phase was stirred for 30 minutes with 6.3 kg water and the phases were separated. 11 kg CPME was evaporated at 100 mbar at 50° C.

The solution was cooled to 0-5° C. and the obtained solid was filtered off using Buchner funnel. The cake was washed with 1 liter of cold water and dried in vacuum oven at 65° C. The product was obtained in 75% isolated yield.

Example 17: Reaction of Compound Having the Formula (IIai) with Dimethylsulphate (DMS) in Absence of Base in DMA 200 gr DMA and 100 gr 5-fluoro-4-imino-1-(toluene-4-sulfonyl)-3,4-dihydro-1H-pyrimidin-2-one (IIai) (81% purity) were added into a 25 L reactor. The mixture was heated to 35° C. and dimethylsulfate was added (110 gr, 2.5 mol equiv.) over 60 minutes. The reaction was stirred for 4 hours at 35-40° C. 50 gr CPME and aqueous solution of $K_2CO_3$ (15% w, 600 gr) was added and the mixture was heated to 60° C. was stirred for 120 minutes at 45° C.

The mixture was cooled to 0-5° C. over 1 hour and the obtained solid was filtered off using Buchner funnel. The cake was mixed with 300 gr water for 1 hour at 40° C., cooled to 0° C., filtered and the process of water slurry repeated again. The product was dried in vacuum oven at 65° C. The product was obtained in 80% isolated yield in 99% purity.

Example 18: Reaction of Compound Having the Formula (IIai) with Dimethylsulphate (DMS) 5 Equiv. in Absence of Base in DMA and CPME 28 gr CPME, 7 gr DMA and 10 gr 5-fluoro-4-imino-1-(toluene-4-sulfonyl)-3,4-dihydro-1H-pyrimidin-2-one (81% purity) were added into a round bottom flask. The mixture was heated to 35° C. and dimethylsulfate was added (18 gr, 5 mol equiv.) over 30 minutes. The reaction was stirred for 5.5 hours at 39° C. 53 gr CPME was added and the mixture was heated to 58° C. until a clear solution was obtained. An aqueous solution of $K_2CO_3$ (10% w) was added and the mixture was stirred for 30 minutes. The phases were separated and the organic phase was mixed with another 176 gr solution of 10% $K_2CO_3$ containing 0.5 gr of TBAB for 1 hour followed by phase separation and repeating the same procedure again. The organic phase was washed with 300 gr of water and then 300 gr of CPME was evaporated at 100 mbar at 50° C.

The solution was cooled to 0-5° C. and the obtained solid was filtered off using Buchner funnel. The cake was washed with 1 liter of cold water and dried in vacuum oven at 65° C. The product was obtained in 99.5% purity and 81% isolated yield.

Example 19: Reaction of Compound Having the Formula (IIai) with Dimethylsulphate (DMS) in Presence of Base in DMA and CPME 5.6 gr CPME, 1.4 gr DMA and 2 gr 5-fluoro-4-imino-1-(toluene-4-sulfonyl)-3,4-dihydro-1H-pyrimidin-2-one (81% purity) were added into a round bottom flask. The mixture was heated to 35° C. and dimethylsulfate was added (2.5 gr, 3.5 mol equiv.) over 30 minutes. The reaction was stirred for 4 hours at 40° C. After 4 hours, $Na_2CO_3$ (0.3 equiv.) was added and the stirring was continued for an additional hour until complete conversion of starting material.

10 gr CPME was added and the mixture was heated to 56° C. until a clear solution was obtained. An aqueous solution of $K_2CO_3$ (10% w) was added and the mixture was stirred for 30 minutes. The phases were separated and the organic phase was mixed with another 35 gr solution of 10% $K_2CO_3$ for 1 hour followed by phase separation and repeating the same procedure again. The organic phase was washed with 60 gr of water and then 60 gr of CPME was evaporated at 100 mbar at 50° C.

The solution was cooled to 0-5° C. and the obtained solid was filtered off using Buchner funnel. The cake was washed with 1 liter of cold water and dried in vacuum oven at 65° C. The product was obtained in 97.5% purity and 74% isolated yield.

Example 20: Reaction of Compound Having the Formula (IIai) with Dimethylsulphate (DMS) in Presence of Base in DMA and CPME 28 gr CPME, 7 gr DMA and 10 gr 5-fluoro-4-imino-1-(toluene-4-sulfonyl)-3,4-dihydro-1H-pyrimidin-2-one (81% purity) were added into a round bottom flask. The mixture was heated to 35° C. and dimethylsulfate was added (12.6 gr, 3.5 mol equiv.) over 30 minutes. The reaction was stirred for 4 hours at 39° C. After 4 hours, NaOMe (0.5 equiv) was added and the stirring was continued for an additional hour until complete conversion of starting material.

53 gr CPME was added and the mixture was heated to 58° C. until a clear solution was obtained. An aqueous solution of $K_2CO_3$ (10% w) was added and the mixture was stirred for 30 minutes. The phases were separated and the organic phase was mixed with another 176 gr solution of 10% $K_2CO_3$ containing 0.5 gr of TBAB for 1 hour followed by phase separation and repeating the same procedure again. The organic phase was washed with 300 gr of water and then 300 gr of CPME was evaporated at 100 mbar at 50° C.

The solution was cooled to 0-5° C. and the obtained solid was filtered off using Buchner funnel. The cake was washed with 1 liter of cold water and dried in vacuum oven at 65° C. The product was obtained in 98.8% purity and 77% isolated yield.

Example 21: Reaction of Compound Having the Formula (IIai) with Dimethylsulphate (DMS) in High Shear Stirring in DMA/CPME 200 gr CPME, 200 gr DMA and 200 gr 5-fluoro-4-imino-1-(toluene-4-sulfonyl)-3,4-dihydro-1H-pyrimidin-2-one (81% purity) were added into a reactor. The mixture was heated to 35° C. and dimethylsulfate was added (266 gr, 3.5 mol equiv.) over 30 minutes. The reaction was stirred for 5.5 hours at 35-40° C. 1/10 of the reaction mixture were taken into a 250 mL reactor equipped with high shear stirrer. 60 gr of CPME was added and the mixture was heated to 60° C. 120 gr aqueous solution of potassium carbonate 15% was added over 10 minutes. The mixture was cooled to 50° C. and the mixture was stirred for 2 hours followed by additional stirring for 2 hours at 30° C. The mixture was cooled to 0° C., filtered using buchner funnel and the cake was dried at 65° C. overnight in vacuum oven. The product was obtained in 97.7% purity and 62% yield.

Example 22: Reaction of Compound Having the Formula (IIai) with Dimethylsulphate (DMS) in DMA and CPME 200 gr CPME, 200 gr DMA and 200 gr 5-fluoro-4-imino-1-(toluene-4-sulfonyl)-3,4-dihydro-1H-pyrimidin-2-one (81% purity) were added into a reactor. The mixture was heated to 35° C. and dimethylsulfate was added (266 gr, 3.5 mol equiv.) over 30 minutes. The reaction was stirred for 5.5 hours at 35-40° C. 193 gr of the reaction mixture were taken into a 1 L reactor equipped with mechanical stirrer. 151 gr of CPME was added and the mixture was heated to 60° C. over 10 minutes. 300 gr aqueous solution of potassium carbonate 15% was added over 20 minutes. The mixture was cooled to 30° C. and the mixture was stirred for 6 hours followed by cooling to 0° C. over 15 minutes. The product was filtered using buchner funnel and the cake was washed with 200 gr water and dried at 65° C. overnight in vacuum oven. The product was obtained in 98.1% purity and 60% yield.

Example 23: Reaction of Compound Having the Formula (IIai) with Dimethylsulphate (DMS) in DMA and CPME 200 gr CPME, 200 gr DMA and 200 gr 5-fluoro-4-imino-1-(toluene-4-sulfonyl)-3,4-dihydro-1H-pyrimidin-2-one (81% purity) were added into a reactor. The mixture was heated to 35° C. and dimethylsulfate was added (266 gr, 3.5 mol equiv.) over 30 minutes. The reaction was stirred for 5.5 hours at 35-40° C. The mixture was heated to 60° C. over 10 minutes and added dropwise into a reactor containing potassium carbonate 15% solution. The mixture was cooled to 30° C. and the mixture was stirred for 3 hours followed by cooling to 0° C. over 1.5 hours. The product was filtered using buchner funnel and the cake was washed with 150 gr water and filtered. the wet cake was mixed with 700 gr of water for 3 hours, filtered and washed with 150 gr water filtered and dried in vacuum oven at 65° C. The product was obtained in 97% purity and 65% yield.

Example 24: Reaction of Compound Having the Formula (IIai) with Dimethylsulphate (DMS) in CPME at 85°

15 gr CPME and 2 gr 5-fluoro-4-imino-1-(toluene-4-sulfonyl)-3,4-dihydro-1H-pyrimidin-2-one (90.7% purity) were added into a round bottom flask. Dimethylsulfate was added (6 gr, 7.4 mol equiv.) in one portion. The reaction was stirred for 3 hours at 85° C. 53% selectivity and 81% conversion of starting material was observed according to HPLC. The product was not isolated.

Example 25: Reaction of Compound Having the Formula (IIai) with Dimethylsulphate (DMS) in CPME/DMA at 25° C.

6 gr CPME, 2 gr DMA and 5 gr 5-fluoro-4-imino-1-(toluene-4-sulfonyl)-3,4-dihydro-1H-pyrimidin-2-one (90.7% purity) were added into a round bottom flask. Dimethylsulfate was added (6 gr, 3 mol equiv.) in one portion. 2 gr 7% NaOH solution was added and the reaction was stirred at room temperature for 6 hours. 60% selectivity and 84% conversion of starting material was observed according to HPLC. The product was not isolated.

Example 26: Reaction of Compound Having the Formula (IIai) with Dimethylsulphate (DMS) in MeTHF Using Triethylamine as Base 10 gr Methyltetrahydrofurane and 5 gr 5-fluoro-4-imino-1-(toluene-4-sulfonyl)-3,4-dihydro-1H-pyrimidin-2-one (90.7% purity) and 0.8 gr triethylamine were added into a round bottom flask. Dimethylsulfate was added (4 gr, 5 mol equiv.) in one portion. The reaction was stirred at 45° C. for 6 hours. 73% selectivity and 81% conversion of starting material was observed according to HPLC. The product was not isolated.

Example 27: Reaction of Compound Having the Formula (IIai) with Dimethylsulphate (DMS) 10 Mol Equiv. in MeTHF 15 gr Methyltetrahydrofurane and 2 gr 5-fluoro-4-imino-1-(toluene-4-sulfonyl)-3,4-dihydro-1H-pyrimidin-2-one (90.7% purity) were added into a round bottom flask. Dimethylsulfate was added (8 gr, 10 mol equiv.) in one portion. The reaction was stirred at 40° C. for 5 hours. 62% selectivity and 70% conversion of starting material was observed according to HPLC. The product was not isolated.

Discussion

There is a need to develop an improved synthetic process for producing 5-(fluoro-4-imino-3-methyl)-1-tosyl-3,4-dihydro-pyrimidine-(1h)-one.

The claimed process is an improvement over the processes described in WO2015/103144 and/or WO2015/103142 for synthesizing 5-(fluoro-4-imino-3-methyl)-1-tosyl-3,4-dihydro-pyrimidine-(1h)-one.

The present invention provides an efficient pathway for synthesis of compound I with two step reaction wherein each step is one step reaction without additional protection group and/or without using the alkylation reaction as described in WO2015/103144 and/or WO2015/103142.

The process is designed to solve the problem of non-selective sulfonation and alkylation steps as described in the previous process.

REFERENCES

WO 2015/103144, published Jul. 9, 2015 (Adama Makhteshim Ltd.)

WO 2015/103142, published Jul. 9, 2015 (Adama Makhteshim Ltd.)

The invention claimed is:

1. A process for preparing the compound 5-fluoro-4-imino-3-methyl-1-(phenyl-4-sulfonyl)-3,4-dihydro-1H-pyrimidin-2-one having formula (I):

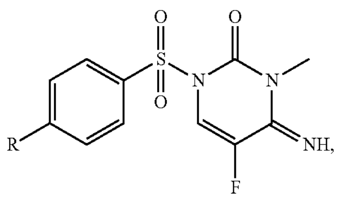

(I)

comprising:

(a) reacting 5-fluorocytosine with compound having formula (III):

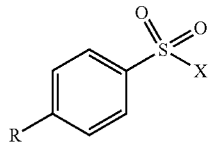

(III)

in the presence of at least one polar solvent and at least one base to obtain the compound having formula (II)

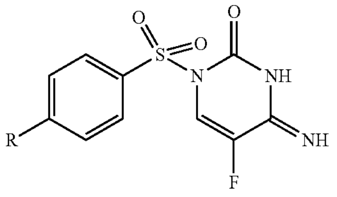

(II)

and (b) reacting the compound having formula (II) with dimethylsulphate (DMS);

wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, —$NH_2$, —$NO_2$, —CN or $CF_3$; and X is a halogen or —$OSO_2PhR$.

2. The process of claim 1, wherein the compound having formula (I) is a compound having formula (Iai):

(Iai)

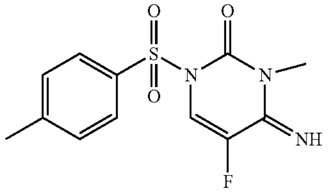

and the process comprises:

(a) reacting 5-fluorocytosine with a compound having formula (III):

(III)

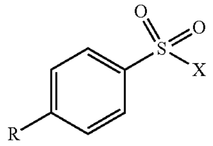

in the presence of at least one polar solvent and at least one base to obtain a compound having formula (IIai)

(IIai)

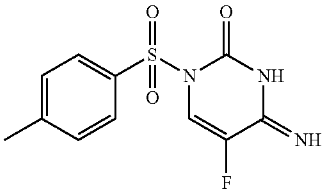

and (b) reacting the compound having formula (IIai) with dimethylsulphate (DMS), wherein R is methyl and X is a halogen or —$OSO_2PhR$.

3. The process of claim 1, wherein:

a) the compound having formula III is 4-toluenesulfonyl chloride (TsCl) or toluenesulfonyl anhydride, b) the reaction of 5-fluorocytosine with the compound having formula (III) is conducted at a temperature between (−5)-85° C., c) the polar solvent has a dielectric constant equal to or above 20, d) the polar solvent of step (a) is selected from the group consisting of dimethyl acetamide (DMA), N-methylpyrolidone (NMP), acetonitrile (ACN or MeCN), dimethylsulfoxide (DMSO), dimethylformamide (DMF), water, and any combination thereof, e) the base of step (a) is selected from a group consisting of $K_2CO_3$, $Na_2CO_3$, $NaHCO_3$, $Li_2CO_3$, $KHCO_3$, NaOH, KOH, $Et_3N$, dimethyl aminopyridine (DMAP), dimethylbenzylamine (DMBA), and any combination thereof, f) in the reaction of 5-fluorocytosine with the compound having formula (III), the molar ratio between 5-fluorocytosine and the compound having formula (III) is between 1:10 to 10:1, g) in the reaction of 5-fluorocytosine with the compound having formula (III), the molar ratio between 5-fluorocytosine and the base is between 1:10 to 10:1, h) in the reaction of 5-fluorocytosine with the compound having formula (III), the molar ratio between the compound having formula (III) and the base is between 1:10 to 10:1, i) the reaction of 5-fluorocytosine with the compound having formula (III) to obtain the compound having formula (II) has a yield higher than 608, and/or j) the reaction of 5-fluorocytosine with the compound having formula (III) to obtain compound having formula (II) further comprises a step of isolating the compound having formula (II) from the reaction mixture, wherein isolation of the compound having formula (II) from the reaction mixture comprises (i) precipitation by adding a protic solvent to the reaction mixture, and (ii) filtration.

4. The process of claim 1, wherein:

a) the reaction of 5-fluorocytosine with the compound having formula (III) is conducted in the presence of (A) two polar solvents, wherein (i) the two polar solvents are DMA and water, and/or (ii) the weight ratio between the two polar solvents is between 10:1 to 1:10, or (B) three polar solvents and the three polar solvents are DMA, water and DMBA, and/or b) the reaction of 5-fluorocytosine with the compound having the formula (III) is conducted in the presence of one base and the base is $K_2CO_3$.

5. The process of claim 1, wherein:

a) the reaction of 5-fluorocytosine with the compound having formula (III) is conducted in the presence of DMA, water and $K_2CO_3$, b) the reaction of 5-fluorocytosine with the compound having formula (III) is conducted in the presence of DMA and $Et_3N$, c) the reaction of 5-fluorocytosine with the compound having formula (III) is conducted in the presence of acetonitrile (ACN or MeCN) and $Et_3N$, d) the reaction of 5-fluorocytosine with the compound having formula (III) is conducted in the presence of DMA, water and DMAP, e) the reaction of 5-fluorocytosine with the compound having formula (III) is conducted in the presence of DMA and $Na_2CO_3$, f) the reaction of 5-fluorocytosine with the compound having formula (III) is conducted in the presence of DMBA and $Na_2CO_3$, g) the reaction of 5-fluorocytosine with the compound having formula (III) is conducted in the presence of water and DMAP, h) the reaction of 5-fluorocytosine with the compound having formula (III) is conducted in the presence of DMA, water, DMBA and KOH, or i) the reaction of 5-fluorocytosine with the compound having formula (III) is conducted in the presence of DMA, water, DMBA and NaOH.

6. The process of claim 1, wherein:

a) the molar ratio between the compound having formula (II) and DMS is between 1:2 to 1:10, b) the reaction of the compound having formula (II) with DMS is conducted at a temperature between 25-85° C., and/or c) the reaction of the compound having formula (II) with DMS to obtain the compound having formula (I) has a yield of at least 60%.

7. The process of claim 1, wherein the reaction of the compound having formula (II) with DMS is conducted in the absence of base.

8. The process of claim 1, wherein the reaction of the compound having formula (II) with DMS is conducted in the presence of at least one base, and wherein:

a) the base is selected from group consisting of DABCO, TBAB, NaOH, $K_2CO_3$, $KHCO_3$, $Na_2CO_3$, $Et_3N$, NaOMe, NaOEt and any combination thereof, b) (i) the base is added at the beginning of the reaction of the compound having formula (II) and DMS, and the temperature of the reaction is above 30° C., or (ii) the base is added after 4 hours from the beginning of the reaction of the compound having formula (II) with DMS and the temperature of the reaction is above 30° C., and/or c) the molar ratio between the compound having formula (II) and the base is 1:0.1 to 1:10.

9. The process of claim 1, wherein:

a) the reaction of the compound having formula (II) with DMS is conducted in the presence of at least one solvent selected from group consisting of DMA, CPME, MeTHE, DMA, DMF, DCM, and any combination thereof, b) the reaction of the compound having formula (II) with DMS is conducted in the presence of two solvents and the two solvents are DMA and CPME, c) the reaction of the compound having formula (II) with DMS is conducted in the presence of one solvent and one base wherein the solvent is MeTHE and the base is $Et_3N$, d) the reaction of the compound having formula (II) with DMS is conducted in the presence of at least one solvent and the molar ratio between the solvent(s) to the compound having formula (II) is between 30:1 and 1:1, and/or e) the reaction of the compound having formula (II) with DMS is conducted in the presence of at least one solvent and the molar ratio between the solvent(s) to DMS is between 10:1 to 1:1.

10. The process of claim 1, wherein the process further comprises a step of isolating the compound having formula (I) from a mixture comprising the compound having formula (I) and DMS, wherein:

a) the compound having formula (I) is isolated by contacting the mixture comprising the compound having formula (I) and DMS with a solvent or a mixture of solvents and filtering the precipitated solid, b) the compound having formula (I) is isolated by (1) washing of an organic solution comprising a polar water immiscible solvent and a mixture of compound (I) and DMS with 2-15% w/w of aqueous basic solution, (2) separating the organic phase from the water phase, and (3) concentrating the organic phase and filtering the precipitated solid, c) the compound having formula (I) is isolated by (1) dissolving the mixture comprising the compound having formula (I) and DMS in an organic polar solvent to obtain an organic solution, (2) washing the organic solution obtained from (1) with 2-15% w/w of aqueous basic solution, (3) separating the organic phase from the water phase, and (4) concentrating the organic phase and filtering the precipitated solid, or d) the compound having formula (I) is isolated by (1) mixing the mixture comprising (i) the compound having formula (I), (ii) DMS and optionally (iii) a solvent with 2-15% w/w of an aqueous basic solution to obtain slurry mixture containing solids, and (2) filtering the precipitated solids.

11. A process for preparing 5-fluoro-4-imino-3-methyl-1-(phenyl-4-sulfonyl)-3,4-dihydro-1H-pyrimidin-2-one having formula (I):

(I)

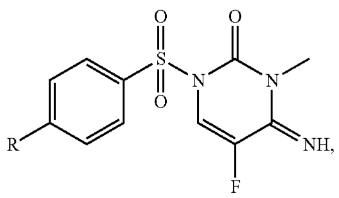

comprising reacting a compound having the formula (II)

(II)

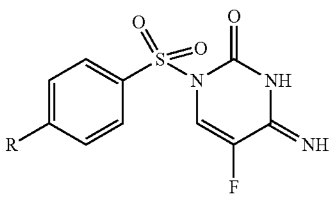

with dimethylsulphate (DMS),
wherein

R is hydrogen, alkyl, alkenyl, alkynyl, alkoxy, haloalkyl, haloalkoxy, alkylthio, haloalkylthio, amino, alkylamino, dialkylamino, alkoxycarbonyl, alkyl carbonyl, hydroxyalkyl, ester, acid halogen, —SH, —OH, $—NH_2$, $—NO_2$, —CN or $CF_3$.

12. The process of claim 11, wherein the 5-fluoro-4-imino-3-methyl-1-(toluene-4-sulfonyl)-3,4-dihydro-1H-pyrimidin-2-one has the formula (Iai)

(Iai)

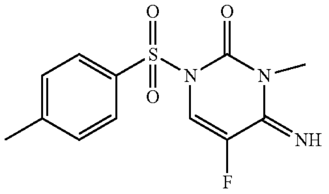

and the process comprises reacting a compound having the formula (IIai)

(IIai)

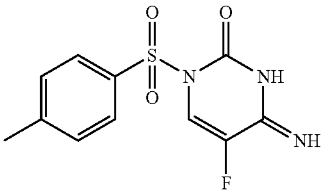

with dimethylsulphate (DMS).

13. The process of claim 1, wherein R is alkyl.

* * * * *